United States Patent
Oshima et al.

(10) Patent No.: US 10,172,971 B2
(45) Date of Patent: Jan. 8, 2019

(54) ABSORBING ARTICLES COMPRISING WATER ABSORBING RESIN AND METHOD FOR PRODUCING THE SAME

(71) Applicant: The Procter & Gamble Company, Cincinnati, OH (US)

(72) Inventors: Kazuyuki Oshima, Himeji (JP); Yoshiro Mitsukami, Himeji (JP); Taku Fujimoto, Himeji (JP); Erina Minami, Himeji (JP); Peter Dziezok, Schwalbach (DE); Marion Lutsche, Schwalbach (DE); Gabriela Schaefer, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 921 days.

(21) Appl. No.: 14/625,644

(22) Filed: Feb. 19, 2015

(65) Prior Publication Data
US 2015/0367018 A1    Dec. 24, 2015

(30) Foreign Application Priority Data

Jun. 23, 2014  (JP) .................. 2014-127898
Aug. 28, 2014  (JP) .................. 2014-174585

(51) Int. Cl.
| | |
|---|---|
| C08F 2/46 | (2006.01) |
| C08G 61/04 | (2006.01) |
| A61L 15/24 | (2006.01) |
| A61F 13/15 | (2006.01) |
| A61F 13/53 | (2006.01) |
| A61L 15/60 | (2006.01) |
| B01J 20/26 | (2006.01) |
| A61L 15/26 | (2006.01) |

(52) U.S. Cl.
CPC ........ *A61L 15/24* (2013.01); *A61F 13/15203* (2013.01); *A61F 13/53* (2013.01); *A61L 15/26* (2013.01); *A61L 15/60* (2013.01); *B01J 20/267* (2013.01); *A61F 2013/15463* (2013.01); *A61F 2013/530226* (2013.01)

(58) Field of Classification Search
CPC .... A61L 15/24; A61L 13/15203; A61L 15/60; A61L 15/26; B01J 20/267; C08L 33/08; A61F 13/53; A61F 2013/15463; A61F 2013/530226; A61F 13/15203
USPC .................. 522/182, 178, 1; 520/1
See application file for complete search history.

(56) References Cited

U.S. PATENT DOCUMENTS

| | | | |
|---|---|---|---|
| 5,607,414 A | 3/1997 | Richards et al. | |
| 5,669,894 A | 9/1997 | Goldman et al. | |
| 5,700,254 A | 12/1997 | McDowall et al. | |
| 6,534,149 B1 | 3/2003 | Daley et al. | |
| 6,992,144 B2 | 1/2006 | Dairoku et al. | |
| 7,786,341 B2 | 8/2010 | Schneider et al. | |
| 8,383,746 B2 | 2/2013 | Torii et al. | |
| 8,802,800 B2 | 8/2014 | Fujino et al. | |
| 8,809,475 B2 | 8/2014 | Matsumoto et al. | |
| 8,875,415 B2 | 11/2014 | Irie | |
| 2002/0137422 A1 | 9/2002 | Graef et al. | |
| 2003/0105190 A1 | 6/2003 | Diehl et al. | |
| 2005/0209352 A1 | 9/2005 | Dairoku et al. | |
| 2007/0123658 A1 | 5/2007 | Torii et al. | |
| 2008/0214749 A1 | 9/2008 | Weismantel et al. | |
| 2009/0208748 A1 | 8/2009 | Torii et al. | |
| 2009/0259016 A1 | 10/2009 | Johnson et al. | |
| 2010/0120940 A1* | 5/2010 | Adachi | A61F 13/15 523/111 |
| 2012/0157644 A1 | 6/2012 | Fujino et al. | |
| 2012/0157648 A1 | 6/2012 | Matsumoto et al. | |
| 2012/0329953 A1 | 12/2012 | Irie | |
| 2017/0158826 A1* | 6/2017 | Oshima | C08G 81/021 |

FOREIGN PATENT DOCUMENTS

| | | |
|---|---|---|
| CN | 1272504 | 11/2000 |
| EP | 0149880 | 7/1985 |
| EP | 2130581 | 12/2009 |
| WO | WO 2008016371 | 2/2008 |
| WO | WO 2011/040530 | 4/2011 |

OTHER PUBLICATIONS

Modern Superabsorbent Polymer Technology, 1998, pp. 55-60, pp. 97-103.
J. A. Johnson et al., J. Am. Chem. Soc., 2006, 128, pp. 6564-6565.
T. Sakai et al., Macromolecules, 2008, 41, pp. 5379-5384.
Chemical Formula A, Scheme 1, J. Am. Chem. Soc., 2006, 128, 14599-14605.
Supporting Information (S2) of J. Am. Chen. Soc. 2007, 129, 12916-12917.
International Search Report, PCT/US2015/016463, dated May 13, 2015, 10 pages.

\* cited by examiner

*Primary Examiner* — Jessica Whiteley
(74) *Attorney, Agent, or Firm* — James T. Fondriest

(57) ABSTRACT

Absorbing articles comprises water absorbing resin including a water-soluble unsaturated monomer, having a dissociable group, as a main component in a repeating unit of a main chain and an internal cross-linked structure, in which a cross-linked structure index represented by the formula [Cross-linked structure index=(Equilibrium swelling capacity with respect to 0.9% by weight of brine)$^{1/3}$/(Weight average molecular weight after hydrolysis treatment)×1,000,000] is 14 or more, a weight average molecular weight after hydrolysis treatment is 220,000 or less, and a molecular weight distribution after hydrolysis treatment is 3.40 or less, and a method for producing the same.

6 Claims, 3 Drawing Sheets

ABSORBING ARTICLES COMPRISING WATER ABSORBING RESIN AND METHOD FOR PRODUCING THE SAME

TECHNICAL FIELD

The present invention relates to absorbing articles comprising water absorbing resin, and a method for producing the same.

DESCRIPTION OF RELATED ART

Hitherto, a water absorbing resin has been used as one of constituent materials of sanitary cotton, disposable diapers, or other sanitary materials absorbing body fluid. Examples of such a water absorbing resin include hydrolysates of starch-acrylonitrile-grafted polymers, neutralized products of starch-acrylic acid-grafted polymers, saponified products of vinyl acetate-acrylic acid ester copolymers, hydrolysates of acrylonitrile copolymers or acrylamide copolymers, and cross-linked bodies thereof or cross-linked bodies of partially-neutralized products of poly(meth)acrylic acid. Among these, from the viewpoint of absorbing properties, a water absorbing resin formed from a cross-linked body of partially-neutralized polyacrylic acid (salt) has been used in many cases. All of these have a cross-linked structure and are insoluble in water.

As desired properties of such a water absorbing resin, a high water absorbing capacity, a high water absorbing speed, an excellent suction force for sucking water from a base material, a high liquid permeability, and the like are exemplified. Among these, the liquid permeability of the water absorbing resin is apprehended as a performance for transporting the added liquid in particles or between particles and three-dimensionally distributing the liquid into a swollen state thereof. In the case of a particulate water absorbing resin, transportation by capillary action in which the liquid passes through gaps between swollen gel particles of the water absorbing resin is main transportation. Hitherto, in a water absorbing resin in which capillary gaps cannot be maintained only by the gel under a load because the gel lacks stability, these materials are held by a fiber matrix and thus mutual separation between particles is secured. However, in a new generation of a diaper structure, a fiber material for supporting the liquid transportation using the water absorbing resin is used in only a small amount or is not used at all. Therefore, it is necessary for the water absorbing resin to be used for the diaper structure to have a sufficiently high stability in a swollen state. In the water absorbing resin, an elastic modulus of the swollen gel is required in order to achieve a high stability in the swollen state.

For the purpose of improving various water absorbing properties of the water absorbing resin such as an elastic modulus of the swollen gel, hitherto, an operation has been performed in which a cross-linked structure is formed in the vicinity of the surface of the water absorbing resin by using a cross-linking agent having a plurality of functional groups which may react with a carboxyl group present in the water absorbing resin so as to improve a surface cross-linking density of the water absorbing resin (surface cross-linking) (Modern Superabsorbent Polymer Technology, 1998, pp. 55-60, pp. 97-103). When an internally-cross-linked body (a base polymer) of partially-neutralized polyacrylic acid before surface cross-linking is synthesized, improvement of the elastic modulus of the swollen gel is also carried out by a technique of adding a chain transfer agent at the time of polymerization (Japanese Patent Application Laid-Open No. 2005-111474) or a technique of increasing an amount of a radical initiator to be used at the time of polymerization (Japanese Patent Application National Publication (Laid-Open) No. 2009-531467). Mechanisms of improving the elastic modulus of the swollen gel in these techniques are considered as follows. That is, by adding a chain transfer agent or increasing an amount of a radical initiator at the time of polymerization, a weight average molecular weight of a main chain polymer in the water absorbing resin can be lowered. According to this, an entangled cross-linking of the main chain polymer is decreased. The entangled cross-linking is to suppress the swelling of the gel. Therefore, in the case of adding a chain transfer agent or increasing an amount of a radical initiator at the time of polymerization, in order to obtain a water absorbing resin having the same equilibrium absorption capacity as that of the water absorbing resin by general polymerization, it is necessary to further increase an amount of an internal cross-linking agent to be used and to compensate for a decrease of entangled cross-linking with chemical cross-linking. As a result, water absorbing resins obtained by these techniques have a reduced proportion of entangled cross-linking with respect to the internal cross-linked structure and an increased proportion of chemical cross-linking, compared to a water absorbing resin obtained by general polymerization. It is believed that a high proportion of chemical cross-linking is important in order to achieve a high elastic modulus of the swollen gel.

However, the weight average molecular weight of the main chain of the water absorbing resin each obtained by these techniques has no considerable difference compared to a general water absorbing resin. Moreover, there is no considerable difference in the amount of a chemical cross-linking agent for achieving the same equilibrium absorption capacity as that of the general water absorbing resin. Therefore, in the cross-linked structure of the water absorbing resin each obtained by these techniques, it is considered that a lot of entangled cross-linking is still present and there is a room for a significant improvement.

However, in this case, it is considered that, only and simply by further decreasing a weight average molecular weight of the main chain and reducing the proportion of the entangled cross-linking, it is not possible to expect achievement of a high elastic modulus of the swollen gel. This is because it is considered that, in order to achieve a high elastic modulus of the swollen gel, it is necessary not only to decrease a weight average molecular weight of the main chain but also to narrow a molecular weight distribution of the main chain from reasons as described below. That is, when one assumes that a water absorbing resin has a small weight average molecular weight of the main chain and a wide molecular weight distribution, a large number of extremely short main chains will be present in the cross-linked structure thereof. Probabilistically, the number of cross-linked sites included in such an extremely short main chain will decrease drastically. When the number of cross-linked sites is small, proportion of the length of the dangling chains with respect to the entire chain length increases. The term "dangling chain" described herein and as used throughout the description indicates a terminal site of the main chain, which is not interposed between two cross-linked sites. In an extreme case, the entire main chain will be a dangling chain when it has only one cross-linked site. Since dangling chains do not contribute to the elastic modulus of the swollen gel, in order to improve the elastic modulus of the swollen gel, it is preferable to decrease dangling chains and to increase elastically effective main chains. Therefore, it is believed that, in order to suppress generation of dangling chains, the molecular weight distribution of the main chain has to be narrowed to prevent generation of extremely short main chains.

From what is described above, if it is possible to obtain a water absorbing resin with a uniform network structure of a uniform mesh size having the main chain with small weight average molecular weight and narrow molecular weight distribution, it is considered that the entangled cross-linking or dangling chain present in the cross-linked structure can be decreased extremely and thus a high elastic modulus of the swollen gel can be exhibited.

Hitherto, syntheses of gels having a uniform network structure of a uniform mesh size have been reported. For example, in J. A. Johnson et al., J. Am. Chem. Soc., 2006, 128, pp. 6564-6565, disclosed is a technique of synthesizing a polyacrylic acid ester cross-linked body having a uniform network structure by performing terminal cross-linking of a linear polymer having functional groups at both terminals by using a star-shaped low molecular weight compound. Moreover, although most of the matters disclosed in J. A. Johnson et al., J. Am. Chem. Soc., 2006, 128, pp. 6564-6565 relate to a polyacrylic acid ester cross-linked body, there is a description on that "the polyacrylic acid ester cross-linked body can be derived into a polyacrylic acid cross-linked body."

Further, as for "synthesis of a nonionic hydrophilic gel having a uniform network structure," there are a large number of known literatures relating to the synthesis of a polyethylene glycol cross-linked body by reaction of two kinds of star-shaped polymers and evaluation of physical properties thereof (for example, T. Sakai et al., Macromolecules, 2008, 41, pp. 5379-5384, and the like).

However, in the related art such as J. A. Johnson et al., J. Am. Chem. Soc., 2006, 128, pp. 6564-6565 or T. Sakai et al., Macromolecules, 2008, 41, pp. 5379-5384, relating to the "synthesis of a gel having a uniform network structure," there is no description on that two or more kinds of star-shaped polymers are reacted with each other to form an ionic network structure.

SUMMARY

The inventors of the present invention found out by their investigation that, in a technique, which has been proposed hitherto, of improving an elastic modulus of a swollen gel by controlling production conditions at the time of producing a base polymer before surface cross-linking, there is a problem in that a swelling capacity originally required for a water absorbing resin is significantly lowered when the elastic modulus of the swollen gel is intended to be increased.

Therefore, the present invention is intended to provide absorbing articles comprising water absorbing resin, the water absorbing resin being capable of exhibiting a high elastic modulus of a swollen gel while maintaining a high swelling capacity, and a method for producing the same.

The inventors of the present invention conducted intensive studies in view of the above-described problems, and as a result, found that the above-described problems may be solved in such a manner that a value of an equilibrium swelling capacity with respect to a physiological saline, a value of a weight average molecular weight (Mw) after a predetermined hydrolysis treatment, and a molecular weight distribution (Mw/Mn) of a water absorbing resin including a water-soluble unsaturated monomer, which has a dissociable group, as a main component in a repeating unit of a main chain and having an internal cross-linked structure are controlled to satisfy a predetermined relation. Therefore, the present invention was completed.

That is, according to the present invention, there is provided absorbing articles comprising water absorbing resin, the water absorbing resin including a water-soluble unsaturated monomer, which has a dissociable group, as a main component in a repeating unit of a main chain and having an internal cross-linked structure, in which a cross-linked structure index represented by the following Mathematical Formula 1 is 14 or more, a weight average molecular weight (Mw) after hydrolysis treatment is 220,000 or less, and a molecular weight distribution (Mw/Mn) after hydrolysis treatment is 3.40 or less:

$$\text{Cross-linked structure index} = (\text{Equilibrium swelling capacity with respect to 0.9\% by weight of brine})^{1/3}/(\text{Weight average molecular weight (Mw) after hydrolysis treatment}) \times 1,000,000 \quad \text{[Mathematical Formula 1]}$$

Here, the hydrolysis treatment is treatment in which 50 mg of the water absorbing resin as a solid content is left to stand still in 10 g of 0.1 mol/l aqueous solution of sodium hydroxide at 80° C. for 3 weeks, and the weight average molecular weight (Mw) is a value obtained by measurement after the treatment.

Further, the inventors of the present invention found a method completely different from a conventionally and generally used method for producing a cross-linked body of partially-neutralized polyacrylic acid (salt), as a method for producing a water absorbing resin capable of exhibiting excellent properties as described above (having a high elastic modulus while maintaining an equilibrium swelling capacity).

That is, according to another aspect of the invention, there is provided a method for producing absorbing articles comprising water absorbing resin, the water absorbing resin including a water-soluble unsaturated monomer, which has a dissociable group, as a main component in a repeating unit of a main chain and having an internal cross-linked structure. The producing method is characterized by including a reaction step of mutually reacting a first star-shaped polymer which includes the water-soluble unsaturated monomer as a main component in a repeating unit of each branched chain and has a first reactive functional group at the terminal of each branched chain and a second star-shaped polymer which includes the water-soluble unsaturated monomer as a main component in a repeating unit of each branched chain and has a second reactive functional group, which can form a chemical bond by mutually reacting with the first reactive functional group, at the terminal of each branched chain.

According to the present invention, there is provided absorbing articles comprising water absorbing resin, the water absorbing resin capable of exhibiting a high elastic modulus of a swollen gel while maintaining a high swelling capacity, and a method for producing the same.

DETAILED DESCRIPTION

Figure 1:
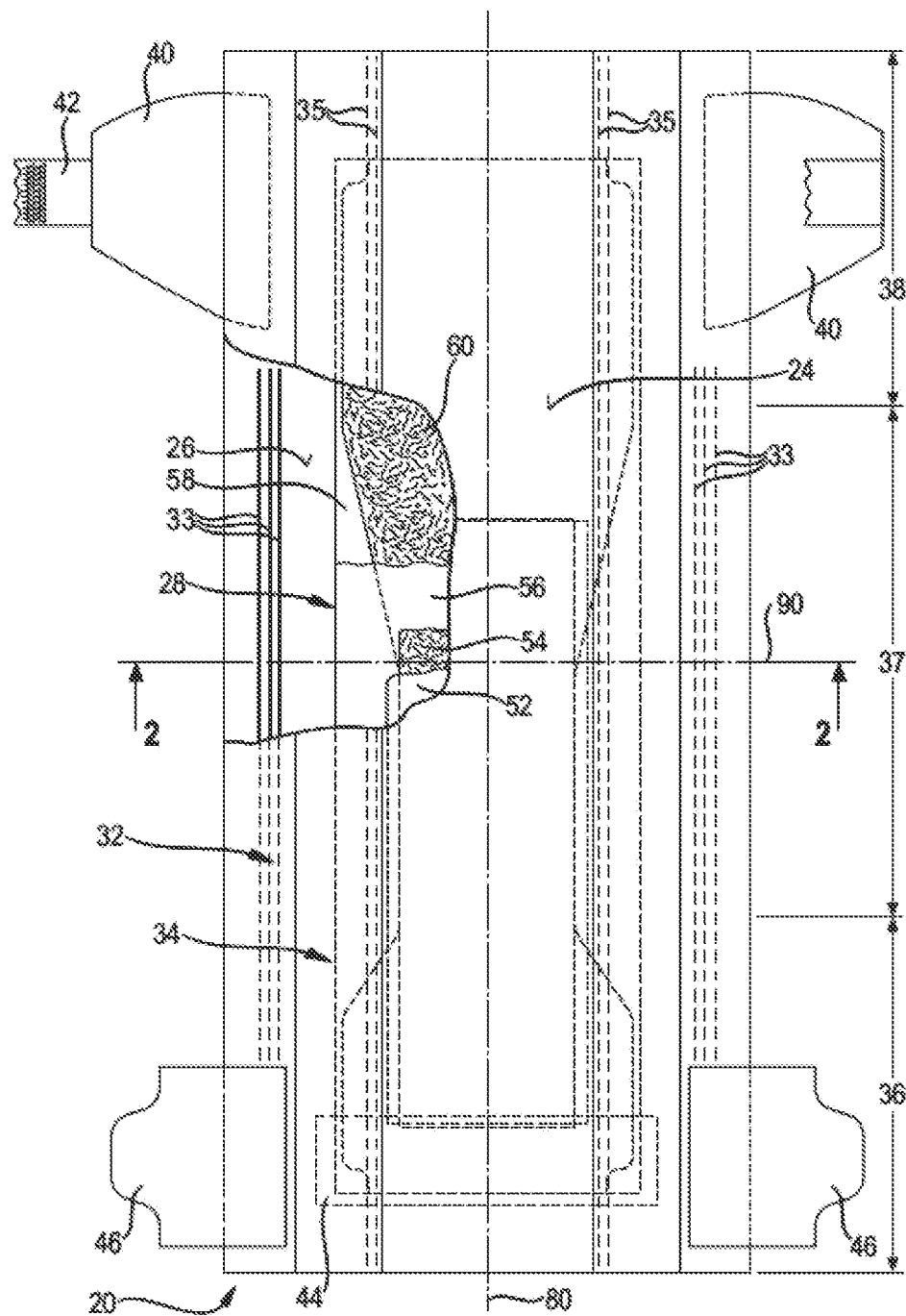
FIG. 1 is a top view of an exemplary absorbing article in the form of a diaper, which may comprise the water absorbing resin particles of the present invention, with some layers partially removed.

Hereinafter, the present invention will be described in detail. However, the scope of the present invention is not intended to be restricted by these descriptions, and in addition to the following examples, the present invention may be appropriately modified and carried out to the extent that the purport of the present invention is not impaired.

[1] Definition of Terms (1-1) Water Absorbing Resin

In the present specification, a "water absorbing resin" means a water-swellable and water-insoluble polymer gelling agent. Incidentally, the term "water-swellable" means that CRC (water absorption capacity without pressure) defined in ERT441.2-02 is 5 [g/g] or more. Moreover, the term "water-insoluble" means that Extr (a water soluble component) defined in ERT470.2-02 is 0 to 50% by mass. Here, the water absorbing resin may be in a powder form, and particularly preferably is a powdery water absorbing resin having a particle size and a moisture content to be described later. The powdery water absorbing resin is referred to as water absorbing resin particles. Incidentally, the term "water absorbing resin" in this specification also includes a water-swollen gel of the polymer gelling agent.

(1-2) "EDANA" and "ERT"

The term "EDANA" is an abbreviated expression for European Disposables and Nonwovens Associations, and "ERT" is an abbreviated expression for the measurement methods of water absorbing resins (EDANA Recommended Test Methods) under the European standards. Incidentally, in the present invention, unless particularly stated otherwise, physical properties of water absorbing resin are measured according to the original literature of ERT (known literature: revised in 2002). Further, when the following measurements to be described as (a) to (d) are performed, in a case where the water absorbing resin is a water-swollen gel, it is preferable to perform the measurements after performing a drying step, which will be described later, to obtain a dried polymer.

(a) "CRC" (ERT441.2-02)

The term "CRC" is an abbreviated expression for Centrifuge Retention Capacity and means the water absorption capacity without pressure (hereinafter, may also be referred to as "absorption capacity"). Specifically, the CRC is an absorption capacity (unit: [g/g]) obtained after 0.200 g of a water absorbing resin in non-woven fabric is freely swollen for 30 minutes in a large excess of 0.9% by mass of aqueous solution of sodium chloride (physiological saline), and then is dehydrated by using a centrifuge separator at 250 G.

(b) "AAP" (ERT442.2-02)

The term "AAP" is an abbreviated expression for Absorption Against Pressure and means the absorption capacity under pressure. Specifically, the AAP is an absorption capacity (unit: [g/g]) obtained after 0.900 g of a water absorbing resin is swollen for 1 hour in 0.9% by mass of aqueous solution of sodium chloride (physiological saline) under a load of 2.06 kPa (0.3 psi).

(c) "SFC"

The term "SFC (physiological saline flow conductivity)" means liquid permeability of 0.69% by weight of aqueous solution of sodium chloride with respect to the water absorbing resin under a load of 2.07 kPa and is measured according to an SFC testing method disclosed in U.S. Pat. No. 5,669,894.

(d) "PSD" (ERT420.2-02)

The term "PSD" is an abbreviated expression for Particle Size Distribution and means a particle size distribution measured by sieve classification. Incidentally, a mass average particle size (D50) and a particle size distribution width are measured by the same method as the method of "Average Particle Diameter and Distribution of Particle Diameter" described in European Patent No. 0349240.

(1-3) Absorbing Article

"Absorbing article" refers to devices that absorb and contain body exudates, particularly urine and other water-containing liquids, and, more specifically, refers to devices that are placed against or in proximity to the body of the wearer to absorb and contain the various exudates discharged from the body. Absorbing articles may include diapers (baby diapers and diapers for adult incontinence), pants, feminine care absorbing articles such as sanitary napkins or pantiliners, breast pads, care mats, bibs, wipes, and the like. As used herein, the term "exudates" includes, but is not limited to, urine, blood, vaginal discharges, breast milk, sweat and fecal matter. Preferred absorbing articles of the present invention are disposable absorbing articles, more preferably disposable diapers and disposable pants.

(1-4) Absorbent Core

"Absorbent core" is used herein to refer to a structure disposed between a topsheet and backsheet of an absorbing article for absorbing and containing liquid received by the absorbing article. If the absorbing article in addition to the absorbing core comprises a topsheet and/or a backsheet, and/or an acquisition system, the absorbing core does not include the topsheet, the backsheet and/or the acquisition system.

(1-5) Air Felt

"Airfelt" is used herein to refer to comminuted wood pulp, which is a form of cellulosic fiber.

(1-6) Disposable

"Disposable" is used in its ordinary sense to mean an article that is disposed or discarded after a limited number of usage events over varying lengths of time, for example, less than 20 events, less than 10 events, less than 5 events, or less than 2 events. If the disposable absorbing article is a diaper, a pant, sanitary napkin, sanitary pad or wet wipe for personal hygiene use, the disposable absorbing article is most often intended to be disposed after single use.

(1-7) Diaper and Pant

"Diaper" and "pant" refers to an absorbing article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant into position about the wearer's lower torso. A pant may be pre-formed by any suitable technique including, but not limited to, joining together portions of the absorbing article using refastenable and/or non-refastenable bonds (e.g., seam, weld, adhesive, cohesive bond, fastener, etc.). A pant may be preformed anywhere along the circumference of the article (e.g., side fastened, front waist fastened). In a diaper, the waist opening and leg openings are only formed when the diaper is applied onto a wearer by (releasable)

attaching the longitudinal edges of the first and second waist region to each other on both sides by a suitable fastening system.

(1-8) Thermoplastic Adhesive Material

"Thermoplastic adhesive material" is used herein to refer to a polymer composition from which fibers may be formed and applied to the water absorbing resin particles with the intent to immobilize the water absorbing resin particles in both the dry and wet state. The thermoplastic adhesive material of the present invention preferably forms a fibrous network over the water absorbing resin particles.

(1-9) Others

In this specification, "X to Y" that indicates a range means "more than or equal to X and less than or equal to Y" including X and Y. Further, the unit of mass, "t (ton)" means "Metric ton." Furthermore, unless particularly stated otherwise, the unit "ppm" means "ppm by mass." Furthermore, the term "-acid (salt)" means "-acid and/or a salt thereof," and "(meth)acryl" means "acryl and/or methacryl." As for measurement of physical properties and the like, unless particularly stated otherwise, the measurement is carried out at room temperature (20 to 25° C.) and a relative humidity of 40 to 50% RH.

[2] Water Absorbing Resin According to Present Invention

According to the present invention, there is provided absorbing articles comprising water absorbing resin, the water absorbing resin including water-soluble unsaturated monomer, which has a dissociable group, as a main component in a repeating unit of a main chain and having an internal cross-linked structure. Further, in the water absorbing resin, a cross-linked structure index represented by the following Mathematical Formula 1 is 14 or more, a weight average molecular weight (Mw) after hydrolysis treatment is 220,000 or less, and a molecular weight distribution (Mw/Mn) after hydrolysis treatment is 3.40 or less.

(2-1) Configuration of Water Absorbing Resin

The water absorbing resin includes a water-soluble unsaturated monomer, which has a dissociable group, as a main component in a repeating unit of a main chain. Here, in this specification, the expression that a monomer "is a main component in a repeating unit" means that a proportion of the monomer with respect to the total repeating unit is 50 mol % or more, and, unless particularly stated otherwise, is preferably 70 mol % or more, more preferably 90 mol % or more, still more preferably 95 mol % or more, particularly preferably 98 mol % or more, and most preferably 99 mol % or more.

The "water-soluble unsaturated monomer having a dissociable group" preferably has a (meth)acrylic acid (salt) as a main component and more preferably has an acrylic acid (salt) as a main component. Examples of the (meth)acrylic acid salt include an alkali metal salt such as a sodium salt, a potassium salt, and a lithium salt of the (meth)acrylic acid salt, an ammonium salt, and an amine salt. An alkali metal salt is preferable and a sodium salt is most preferable.

Examples of the monomer which is used as the "water-soluble unsaturated monomer having a dissociable group," other than a (meth)acrylic acid (salt), include anionic unsaturated monomers such as maleic acid, vinyl sulfonic acid, styrene sulfonic acid, 2-(meth)acrylamide-2-methylpropane sulfonic acid, 2-(meth)acryloylethane sulfonic acid, and 2-(meth)acryloylpropane sulfonic acid.

Further, the water absorbing resin has the "water-soluble unsaturated monomer having a dissociable group" as a main component in a repeating unit of a main chain as described above, but may include a "water-soluble unsaturated monomer having no dissociable group" as a repeating unit of the main chain. Examples of such a monomer include nonionic hydrophilic group-containing unsaturated monomers such as acrylamide, methacrylamide, N-ethyl (meth)acrylamide, N-n-propyl (meth)acrylamide, N-isopropyl (meth)acrylamide, N,N-dimethyl (meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloylpiperidine, N-acryloylpyrrolidine, and N-vinylacetamide; and cationic unsaturated monomers such as N,N-dimethylaminoethyl (meth)acrylate, N,N-diethylaminoethyl (meth)acrylate, N,N-dimethylaminopropyl (meth)acrylate, and N,N-dimethylaminopropyl (meth)acrylamide, and quaternary salts thereof.

Here, the above-described water-soluble unsaturated monomer may be used alone, or two or more kinds thereof may be appropriately used in combination.

In the water absorbing resin according, a ratio of the repeating unit derived from the water-soluble unsaturated monomer having a carboxylic acid (salt) group as a dissociable group with respect to the repeating unit of the main chain is preferably 70 mol % or more, more preferably 80 mol % or more, and still more preferably 90 mol % or more (provided that, the upper limit is 100 mol %). In addition, a ratio of the repeating unit derived from acrylic acid (salt) with respect to the repeating unit of the main chain is preferably 70 mol % or more, more preferably 80 mol % or more, and still more preferably 90 mol % or more (provided that, the upper limit is 100 mol %). Moreover, the repeating unit of the main chain of the water absorbing resin is preferably in a range of 0 to 50 mol % of acrylic acid and 100 to 50 mol % of acrylic acid salt (provided that, the total amount of both is 100 mol % or less) and more preferably in a range of 10 to 40 mol % of acrylic acid and 90 to 60 mol % of acrylic acid salt (provided that, the total amount of both is 100 mol % or less), as constituent units thereof. Incidentally, a molar ratio of the acrylic acid salt to the total amount of the acrylic acid and the acrylic acid salt is referred to as a "neutralization ratio." The value of the neutralization ratio is preferably 50 to 100 mol %.

The water absorbing resin is a cross-linked polymer having an internal cross-linked structure. As a method of introducing an internal cross-linked structure into the water absorbing resin, as described in the section of "Method for Producing Water Absorbing Resin" according to another aspect of the present invention to be described later, a method is exemplified in which two (or more) kinds of star-shaped polymers each having reactive functional groups at the terminals of the branched chain are allowed to react with each other, where the repeating unit of the branched chain mainly consists of a water-soluble unsaturated monomer serving as a repeating unit of the main chain of the water absorbing resin.

(2-2) Cross-Linked Structure Index

The water absorbing resin is characterized in that a cross-linked structure index represented by the following Mathematical Formula 1 is 14 or more, a weight average molecular weight after hydrolysis treatment is 220,000 or less, and a molecular weight distribution (Mw/Mn) after hydrolysis treatment is 3.40 or less:

Cross-linked structure index=(Equilibrium swelling capacity with respect to 0.9% by weight of brine)$^{1/3}$/(Weight average molecular weight (Mw) after hydrolysis treatment)×1,000,000      [Mathematical Formula 1]:

Here, the hydrolysis treatment is treatment in which 50 mg of the water absorbing resin as a solid content is left to stand still in 10 g of 0.1 mol/l aqueous solution of sodium hydroxide at 80° C. for 3 weeks, the weight average molecular weight (Mw) is a value obtained by measurement after the treatment, and an operation for this measurement will be described in detail in the section of Examples to be described later.

The cross-linked structure index has to be 14 or more, but is preferably 30 or more, more preferably 60 or more, still more preferably 90 or more, particularly preferably 120 or more, and most preferably 170 or more. The upper limit of the cross-linked structure index is not particularly limited, but is preferably 1,000 or less. When the cross-linked structure index is more than 1,000, there is a concern that a manufacturing cost of the water absorbing resin is too high. In addition, the weight average molecular weight (Mw) after the above-described hydrolysis treatment has to be 220,000 or less, but is preferably 150,000 or less, more preferably 100,000 or less, still more preferably 50,000 or less, and particularly preferably 25,000 or less. The lower limit of the weight average molecular weight (Mw) after hydrolysis treatment is not particularly limited, but is preferably 10,000 or more. When the weight average molecular weight (Mw) after hydrolysis treatment is less than 10,000, there is a concern that a manufacturing cost of the water absorbing resin is too high. Moreover, the molecular weight distribution (Mw/Mn) after the above-described hydrolysis treatment has to be 3.40 or less, but is preferably 2.50 or less, more preferably 1.80 or less, still more preferably 1.45 or less, and particularly preferably 1.15 or less (provided that, the lower limit is 1.00). According to the investigation of the inventors of the present invention, they found that, when the cross-linked structure index is 14 or more, the weight average molecular weight (Mw) after hydrolysis treatment is 220,000 or less, and the molecular weight distribution (Mw/Mn) after hydrolysis treatment is 3.40 or less, it is possible to provide a water absorbing resin capable of exhibiting a high elastic modulus of the swollen gel while maintaining a high swelling capacity. As a mechanism in which effects as described above is achieved by employing the configuration according to the present invention, a mechanism as described below is assumed. That is, a predetermined value or more of the cross-linked structure index means that the equilibrium swelling capacity is large, the weight average molecular weight is small, and there is little entangled cross-linking. In addition, a narrow molecular weight distribution means that there are few extremely short main chains and a proportion of the dangling chain is small. As also described in the above section of "Description of Related Art," when water absorbing resins having the similar equilibrium absorption capacity are compared, the elastic modulus of the swollen gel is considered to be high for the resin in which the proportion of entangled cross-linking is small, the proportion of chemical cross-linking is large, and the number of the dangling chains not contributing to gel elasticity is small. Therefore, when the cross-linked structure index is 14 or more, the weight average molecular weight after hydrolysis treatment is 220,000 or less, and the molecular weight distribution (Mw/Mn) after hydrolysis treatment is 3.40 or less, it is possible to obtain a water absorbing resin having little entangled cross-linking or dangling chains in the cross-linked structure and exhibiting a high elastic modulus of a swollen gel while maintaining a high swelling capacity. Incidentally, operations for measuring parameters thereof will be described in detail in the section of EXAMPLES to be described later.

[3] Method for Producing Absorbing Articles Comprising Water Absorbing Resin According to Present Invention (3-1) Overview According to the present invention, there is also provided an example of a method for producing the absorbing articles comprising the water absorbing resin according to the present invention described above in [2]. That is, a technical scope of the invention according to the absorbing articles comprising the water absorbing resin of the present invention described above in [2] is not limited only to the absorbing articles comprising the water absorbing resin produced by the producing method to be described below.

As described above, in an example of the method for producing a absorbing articles comprising water absorbing resin according to the present invention, a method is exemplified in which two (or more) kinds of star-shaped polymers each having reactive functional groups at the terminals of the branched chain are allowed to react each other, where the repeating unit of the branched chain mainly consists of a water-soluble unsaturated monomer serving as a repeating unit of the main chain of the water absorbing resin.

That is, there is provided a method for producing a water absorbing resin including a water-soluble unsaturated monomer, which has a dissociable group, as a main component in a repeating unit of a main chain and having an internal cross-linked structure. Further, the producing method is characterized by including a reaction step of mutually reacting a first star-shaped polymer which includes the water-soluble unsaturated monomer as a main component in a repeating unit of each branched chain and has a first reactive functional group at the terminal of each branched chain and a second star-shaped polymer which includes the water-soluble unsaturated monomer as a main component in a repeating unit of each branched chain and has a second reactive functional group, which may form a chemical bond by mutually reacting with the first reactive functional group, at the terminal of each branched chain.

(3-2) Reaction Step

The reaction step is a step of reacting the first star-shaped polymer with the second star-shaped polymer. Further, depending on circumstances, in the reaction step, three or more kinds of star-shaped polymers may be reacted with one another. Here, the term "star-shaped polymer" means a branched polymer having a structure in which an atom or atom group is a core and three or more branched chains extend radially. Incidentally, as for the "star-shaped polymer," literatures such as "Shinpan Koubunshi Jiten (New Polymer Dictionary)" (edited by Koubunshi Jiten Editorial Committee in The Society of Polymer Science, Japan, published by Asakura Publishing Co., Ltd.) or "Daigakuin Koubunshi Kagaku (Polymer Chemistry for Graduated School) (KS Chemistry Specialized Book)" (edited by Takuhei NOSE et al., published by KODANSHA LTD.) may be referenced.

In the producing method, the first star-shaped polymer and the second star-shaped polymer (and third, fourth, . . . star-shaped polymers to be used as necessary) have a water-soluble unsaturated monomer having a dissociable group, as a main component in a repeating unit of each branched chain.

Here, as for the preferred "water-soluble unsaturated monomer having a dissociable group" forming a main component in a repeating unit of the branched chain of the star-shaped polymer, and a water-soluble unsaturated monomer which may be used other than the "water-soluble unsaturated monomer having a dissociable group," the same as described in the section of "(2-1) Configuration of Water Absorbing Resin" may be employed and thus the detail description thereof will not be presented here. In other words, in the producing method, it is also preferable that 90 mol % or more of the repeating unit of each branched chain of the star-shaped polymer be a repeating unit derived from acrylic acid (salt).

Further, in the present invention, the number of branched chains with respect to one core of the star-shaped polymer is not particularly limited, but is preferably 3 to 100, more preferably 3 to 10, and particularly preferably 4. When all of the plurality of star-shaped polymers to be used in the reaction step have four branched chains, each star-shaped polymer has a regular tetrahedron structure. As a result, an internal cross-linked structure to be obtained is a diamond structure. Since a water absorbing resin having such a diamond structure as an internal cross-linked structure has higher network uniformity and exhibits a high elastic modulus of the swollen gel, it can be said that the water absorbing resin is particularly preferable. In other words, it is preferable that the above-described star-shaped polymer have a structure to which a polymer including a water-soluble unsaturated monomer having the dissociable group, as a main component in the repeating unit, is bound, as the branched chain of the four-arm core.

Each star-shaped polymer has a reactive functional group at the terminal of each branched chain. The reactive functional group present at the terminal of each branched chain of each star-shaped polymer has to be a reactive functional group which may form a chemical bond by mutually reacting with a reactive functional group present at the terminal of each branched chain of at least another one of star-shaped polymers. For example, in the case of using only two kinds of star-shaped polymers as exemplified in the section of EXAMPLES to be described later as a star-shaped polymer, a reactive functional group present at the terminal of each branched chain of the second star-shaped polymer (also referred to as a "second reactive functional group") has to be a reactive functional group which may form a chemical bond by mutually reacting with a reactive functional group present at the terminal of each branched chain of the first star-shaped polymer (also referred to as a "first reactive functional group"). Incidentally, reactive functional groups present at the terminal of each of three or more (preferably four) branched chains configuring one star-shaped polymer may be the same as or different from each other, but is preferably the same as each other.

A combination of reactive functional groups present at the terminal of each branched chain of each star-shaped polymer, which is typified by a combination of the first reactive functional group and the second reactive functional group, is not particularly limited, but a combination of arbitrary reactive functional groups may be used as long as it does not react with a site other than the reactive functional group such as a core or a branched chain configuring the star-shaped polymer when the reactive functional groups react with each other in the reaction step. Specific examples of such a combination of reactive functional groups (the first reactive functional group; the second reactive functional group) include (an azido group; an alkynyl group), (a thiol group; an alkenyl group), (a hydrosilyl group; an alkenyl group), (a conjugated diene group; an alkenyl group), and (an amino group; an NHS activated ester group). Among these, from the viewpoint of the functional group selectivity of reaction, a combination of (an azido group; an alkynyl group) may be preferably used.

A technique for obtaining a star-shaped polymer is not particularly limited, but may be appropriately referred to any knowledge in the related art. As an example, in order to obtain a star-shaped polymer, first, an atom or atom group configuring a core is prepared. As a core, an arbitrary polyfunctional compound or a compound modifying it may be used. Examples of the polyfunctional compound include polyols such as pentaerythritol, trimethylolpropane, arabitol, and mannitol; and polyamines such as triethylenetetramine A valence (the number of branched chains) of the star-shaped polymer to be obtained is decided depending on a valence of the atom or atom group as the core to be prepared at this time. For example, when pentaerythritol that is quadrivalent polyol is used as a core, a (quadrivalent) star-shaped polymer having four branched chains can be obtained. In addition, as a modifying operation of a polyfunctional compound, for example, an operation in which esterification is performed by reacting an acyl compound to a functional group included in a polyfunctional compound (in this example, a hydroxy (—OH) group), as described in the section of "Synthesis of Four-Arm Star-Shaped Core" of EXAMPLES to be described later, is exemplified. When the polyfunctional compound is modified in this way, the synthesis reaction of the main chain subsequent to the modification can be allowed to proceed favorably.

Subsequently, the synthesis reaction (polymerization reaction) of the main chain in the branched chain configuring a star-shaped polymer is performed using the core prepared above. As for the polymerization reaction, conventionally known techniques (radical polymerization, cationic polymerization, anionic polymerization, chain polymerization such as living radical polymerization, living cationic polymerization, and living anionic polymerization, or condensation polymerization) can be used, but among these, chain polymerization is preferably used and radical polymerization or living radical polymerization is particularly preferably used.

At this time, in the synthesis reaction (polymerization reaction) of the main chain of the branched chain configuring the star-shaped polymer, the reaction is performed using a monomer component including a water-soluble unsaturated monomer having a dissociable group, as a main component. However, it is preferable that the dissociable group of the water-soluble unsaturated monomer having the dissociable group included in the monomer component to be used for the reaction be protected by a protective group. For example, in a case where the synthesis reaction (polymerization reaction) of the main chain of the branched chain is performed using a monomer component including acrylic acid (salt), which has a carboxy group as a dissociable group, as a main component, it is preferable that a carboxy group serving as a dissociable group be protected using a protective group such as a tert-butyl ester group, a methyl ester group, or an amide group. When the dissociable group is protected by a protective group in this way and then a deprotection step is performed after the reaction step of reacting a plurality of star-shaped polymers with each other, the dissociable group does not influence the reaction of the star-shaped polymers in the reaction step, which is preferable. Incidentally, in the producing method, the "star-shaped polymer" to be used as a reaction material is a polymer including the "water-soluble unsaturated monomer having a dissociable group" as a main component in a repeating unit of each branched chain. However, in this specification, the concept of the "water-soluble unsaturated monomer having a dissociable group" also includes a monomer in which the dissociable group as described above is protected by a protective group.

It is preferable that a step of introducing a reactive functional group (the first reactive functional group) to the terminal of each branched chain of each star-shaped polymer be performed after the synthesis reaction (polymerization reaction) of the main chain of the branched chain is performed in this way. A specific technique for executing the step is not also particularly limited, but may be referred to any knowledge in the related art as appropriate according to the kinds of reactive functional groups to be introduced. For example, in a case where a halogen atom such as a chlorine atom, a bromine atom, or an iodine atom is bound at the terminal of each branched chain at the time point at which the synthesis reaction (polymerization reaction) of the main chain of the branched chain is terminated, it is possible to obtain a star-shaped polymer in which an azide group is introduced to the terminal of each branched chain by causing sodium azide ($NaN_3$) to act as a nucleophile to substitute the halogen atom. Here, the introduction of the reactive functional group to the terminal of each branched chain may be performed by the reaction of two or more stages. For example, by performing a series of reaction as described in the sections of "Synthesis of Dialkyne," "Synthesis of Four-Arm Star-Shaped Polymer (1-Si Alkyne)," and "Synthesis of Four-Arm Star-Shaped Polymer (1-H Alkyne)," it is possible to obtain a star-shaped polymer in which an alkynyl group is introduced to the terminal of each branched chain.

The weight average molecular weight (Mw) of the star-shaped polymer thus obtained is not particularly limited, and is preferably 1,000 or more, more preferably 2,000 or more, still more preferably 5,000 or more, and particularly preferably 10,000 or more in order to obtain a water absorbing resin having a sufficiently large equilibrium swelling capacity. Incidentally, the measuring method of the weight average molecular weight (Mw) of the star-shaped polymer will be described in detail in the section of EXAMPLES to be described later.

In the reaction step, the reaction conditions (a reaction temperature, a reaction time, a reaction solvent, and an equivalent relationship between star-shaped polymers) when the first star-shaped polymer and the second star-shaped polymer (and further the third, fourth, . . . star-shaped polymers) are allowed to react with each other can be set by those skilled in the art as appropriate according to the kinds of reactive functional groups to be used or reaction types caused by the kinds of reactive functional groups to be used, in the light of any knowledge in the related art. For example, in a case where an azido group is used as the first reactive functional group and an alkynyl group is used as the second reactive functional group, it is possible to form a chemical bond having a 1,2,3-triazole structure between the branched chain of the first star-shaped polymer and the branched chain of the second star-shaped polymer by performing cycloaddition reaction in the presence of a copper catalyst. In this case, a range of the reaction temperature is preferably 0 to 100° C. and a range of the reaction time is preferably 1 minute to 96 hours. Further, examples of the reaction solvent include organic solvents such as ethers, for example, diethyl ether; esters, for example, ethyl acetate; halogenated hydrocarbons, for example, dichloromethane; nitriles, for example, acetonitrile; ketones, for example, acetone; and sulfoxides, for example, dimethyl sulfoxide; or aqueous solvents such as water. As for the equivalent relationship between reactants, a range of the second reactive functional group with respect to 1 mol equivalent of the first reactive functional group is preferably 0.80 to 1.20 mol equivalent, and most preferably 1.00 mol equivalent.

As described above, the reaction step of the producing method is preferably performed in a state where the dissociable group of the water-soluble unsaturated monomer, which forms the branched chains of the first star-shaped polymer and the second star-shaped polymer (and the third, fourth, . . . star-shaped polymers), is protected by a protective group. In this case, in general, a step of deprotecting a dissociable group after completion of the reaction step is further included. For example, in the case of using a tert-butyl group as a protective group of a carboxy group serving as a dissociable group, by performing the deprotection reaction using trifluoroacetic acid, the carboxy group serving as a dissociable group is liberated and thus it is possible to obtain a water absorbing resin including a water-soluble unsaturated monomer (for example, acrylic acid), which has a dissociable group, as a main component in a repeating unit of a main chain and having an internal cross-linked structure The neutralization step is performed using a base such as sodium (hydrogen) carbonate, or sodium hydroxide on the water absorbing resin thus obtained and thus it is possible to finally obtain a water absorbing resin having a desired neutralization ratio.

(3-3) Other Steps

In the producing method, for example, a water absorbing resin in a water-swollen gel state may be a final target product as a result of the completion of the neutralization step. However, depending on circumstances, in a manner similar to the water absorbing resin of the related art, post-steps such as drying, pulverization, classification, and surface cross-linking may be carried out. Hereinafter, each step will be described in detail.

(Drying)

In a case where the water absorbing resin obtained in the above-described reaction step (and the neutralization step) is a water-swollen gel, the water absorbing resin may generally be pulverized into a dried polymer before and/or after drying. Incidentally, in this specification, the term "drying" means a step of drying a water-swollen gel until a desired moisture content is achieved and thus obtaining a dried polymer. The moisture content is measured according to the EDANA method (ERT430.2-02) in such a manner that an amount of a sample is set to 1.0 g, the drying temperature is set to 180° C., and the drying time is set to 4 hours. The moisture content is preferably 20% by weight or less, more preferably 1 to 15% by weight, still more preferably 2 to 10% by weight, and particularly preferably 3 to 8% by weight.

The drying method of the water-swollen gel is not particularly limited, and examples thereof include heating drying, hot air drying, drying under reduced pressure, fluidized bed drying, infrared drying, microwave drying, drum dryer drying, dehydration drying by azeotropy with a hydrophobic organic solvent, high humidity drying by using water vapor at a high temperature, and the like. Among these, from the viewpoint of drying efficiency, hot air drying is preferable and band drying in which hot air drying is performed on a through-circulation belt is more preferable.

The drying temperature (the temperature of hot air) in the hot air drying is preferably 120 to 250° C. and more preferably 150 to 200° C., from the viewpoint of the color hue of the water absorbing resin or drying efficiency. As for drying conditions other than the drying temperature, such as a wind speed of hot air or a drying time, they may be set as appropriate according to a moisture content or total weight of a particulate water-containing gel to be provided for drying and a target resin solid content. When band drying is performed, various conditions described in International Publication Nos. WO 2006/100300, WO 2011/025012, WO 2011/025013, and WO 2011/111657 are appropriately employed.

(Pulverization and Classification) It is preferable that the dried polymer obtained in the drying step be pulverized by a pulverizer. Examples of the pulverizer include, although not particularly limited, a roll type pulverizer such as a roll mill, a hammer type pulverizer such as a hammer mill, an impact type pulverizer, a cutter mill, a turbo grinder, a ball mill, and a flush mill. Among these, a roll mill is preferably used to control a particle size distribution. In order to control a particle size distribution, pulverization may be sequentially performed twice or more but preferably three times or more. In a case where pulverization is performed twice or more, pulverizers to be used at each time may be the same as or different from each other. Different types of pulverizers may be used in combination thereof.

In order to control the pulverized water absorbing resin to have a predetermined particle size distribution, classification is preferably performed by a sieve having a specific pore size. A classifier is not particularly limited, but examples of the classifier which is used include a shaking sieve (an unbalanced weight driving type, a resonance type, a vibration motor type, an electromagnetic type, a circle type vibrating type, or the like), an in-plane motion sieve (a horizontal motion type, a horizontal circular-linear motion type, a three-dimensional motion type, or the like), a movable net type sieve, a compulsory stirring type sieve, a net vibrating type sieve, a wind-power sieve, and an acoustic sieve. The shaking sieve and the in-plane motion sieve are preferably used. A pore size of sieve is preferably in a range of 1000 μm to 300 μm, more preferably in a range of 900 μm to 400 μm, and most preferably in a range of 710 μm to 450 μm. When the pore size is not in the above range, there is a possibility that a target particle size distribution cannot be obtained.

In order to control the water absorbing resin according to the present invention to have a specific particle size distribution, some or all of particles having a particle size less than a specific particle size may be removed by further performing classification. In this step, a classifier is not particularly limited. However, classifiers exemplified above are preferably used. In addition to this, an ultrafine classifier (a centrifugal type, an inertial type, or the like) and the like may be used. In this step, some or all of particles having a particle size of preferably less than 200 μm, more preferably less than 150 μm, and most preferably less than 106 μm, are removed.

The shape of the water absorbing resin obtained by each step described above is generally a single particle shape such as an irregular pulverized shape, a spherical shape, a fibrous shape, a rod shape, a substantially spherical shape, or a flat shape, or a granulated particle shape. Since immobilization can be easily performed, for example, when the water absorbing resin is used for a water absorbing body, an irregular pulverized shape or granulated particle shape is preferable. Further, as for a proportion of particles having an irregular pulverized shape or granulated particle shape in the water absorbing resin, the total number is preferably 50% or more, more preferably 70% or more, and still more preferably 90% or more in terms of the number ratio. Incidentally, the shape can be determined visually (including the case of visually determining an enlarged image by a microscope or the like). As for the number ratio, it is not necessary to measure the total number, but the number ratio can be obtained in such a manner that 10 sets of approximately 100 particles are sampled while moving a sampling place and then an arithmetic mean value of each measurement result, that is, approximately 1,000 particles in total are measured.

(Surface Cross-Linking)

The vicinity of the surface of the water absorbing resin according to the present invention is preferably subjected to surface cross-linking by an organic surface cross-linking agent and/or a water-soluble inorganic surface cross-linking agent, each of which is a surface cross-linking agent. In other words, the method for producing a water absorbing resin of the present invention preferably includes a step of performing surface cross-linking on the dried water absorbing resin.

When the vicinity of the surface of the water absorbing resin is subjected to surface cross-linking by a surface cross-linking agent, it is possible to reduce an amount of liquid squeezed out when a pressure is applied to the swollen water absorbing resin. Therefore, AAP or SFC can be increased. As a result, when the water absorbing resin is used for a water absorbing body, it is possible to obtain a water absorbing body having little amount of liquid squeezed out (so-called Re-Wet) when a pressure is applied, and excellent speed of liquid absorption into the water absorbing body.

Examples of the surface cross-linking agent, which can be used for the surface cross-linking treatment, include an organic surface cross-linking agent and/or a water-soluble inorganic surface cross-linking agent, each of which contains two or more functional groups that may react with a functional group contained in the water absorbing resin, particularly a carboxyl group. Preferably, a water-soluble organic surface cross-linking agent can be used.

Examples thereof include polyhydric alcohols such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerine, polyglycerine, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, an oxyethylene-oxypropylene block copolymer, pentaerythritol, and sorbitol; epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; polyvalent amine compounds such as ethylenediamine, diethylenetriamine, triethylenetetramine, tetraethylenepentamine, pentaethylenehexamine, and polyethyleneimine, and its inorganic or organic salt (for example, azetidinium salt or the like); polyvalent isocyanate compounds such as 2,4-tolylene diisocyanate and hexamethylene diisocyanate; polyvalent oxazoline compounds such as 1,2-ethylene bisoxazoline; carbonic acid derivatives such as urea, thiourea, guanidine, dicyandiamide, and 2-oxazolidinone; alkylene carbonate compounds such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, and 1,3-dioxopane-2-one; haloepoxy compounds such as epichlorohydrin, epibromhydrin, and α-methylepichlorohydrin, and its polyvalent amine additives (for example, Kymene produced by Hercules Inc.: registered trademark); silane coupling agents such as γ-glycidoxypropyltrimethoxysilane and γ-aminopropyltriethoxysilane; and oxetane compounds such as 3-methyl-3-oxetanemethanol, 3-ethyl-3-oxetanemethanol, 3-butyl-3- oxetanemethanol, 3-methyl-3-oxetaneethanol, 3-ethyl-3-oxetaneethanol, 3-butyl-3-oxetaneethanol, 3-chloromethyl-3-methyloxetane, 3-chloromethyl-3-ethyloxetane, and polyvalent oxetane compounds.

One kind of the surface cross-linking agents may be used alone, or two or more kinds thereof may be used in combination. Among these, polyhydric alcohols are preferable from the viewpoint in that safeness is high and hydrophilicity of the surface of the water absorbing resin can be improved.

The used amount of the surface cross-linking agent is preferably 0.001 part by mass or more but 5 parts by mass or less with respect to 100 parts by mass of the solid content of the water absorbing resin.

Water may be used in mixing the surface cross-linking agent and the water absorbing resin. The used amount of water is preferably in a range of more than 0.5 part by mass and 10 parts by mass or less and more preferably in a range of 1 part by mass or more but 5 parts by mass or less, with respect to 100 parts by mass of the solid content of the water absorbing resin.

When the surface cross-linking agent or an aqueous solution thereof and the water absorbing resin are mixed, a hydrophilic organic solvent or a third material may be used as a mixing auxiliary agent. In the case of using a hydrophilic organic solvent, examples thereof include lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and methoxy (poly)ethylene glycol; amides such as ε-caprolactam and N,N-dimethylformamide; sulfoxides such as dimethyl sulfoxide; and polyhydric alcohols such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,3-butanediol, 1,4-butanediol, 1,5-pentanediol, 1,6-hexanediol, 1,2-cyclohexane dimethanol, 1,2-cyclohexanol, trimethylolpropane, diethanolamine, triethanolamine, polyoxypropylene, an oxyethylene-oxypropylene block copolymer, pentaerythritol, and sorbitol.

The used amount of the hydrophilic organic solvent varies depending on kinds, particle sizes, the moisture content, or the like of the water absorbing resin. However, the used amount of the hydrophilic organic solvent is preferably 10 parts by mass or less and more preferably in a range of 0 part by mass or more but 5 part by mass or less, with respect to 100 parts by mass of the solid content of the water absorbing resin.

Further, the third material may be inorganic acid, organic acid, polyamino acid, or the like described in the specification of European Patent No. 0668080. These mixing auxiliary agents may act as a surface cross-linking agent, but preferably should not lower the water absorption capability of the water absorbing resin after the surface cross-linking. The water absorbing resin according to the present invention is preferably cross-linked by mixing the resin with a surface cross-linking agent containing no hydrophilic organic solvent of which the boiling point is 100° C. or lower and then heating the mixture. When the water absorbing resin contains a hydrophilic organic solvent of which the boiling point is 100° C. or lower, there is a concern that the hydrophilic organic solvent vaporizes, the environment in which the surface crosslinking agent resides on the surface of the water absorbing resin is changed, and thus physical properties such as SFC (physiological saline flow conductivity) are not sufficiently satisfied.

When the surface cross-linking agent is mixed with the water absorbing resin, preferably, a water-soluble inorganic salt (preferably, a persulfate) is present in order to obtain a more uniform mixture of the water absorbing resin and the surface cross-linking agent. The used amount of the water-soluble inorganic salt varies depending on the kind, the particle size, or the like of the water absorbing resin. However, the used amount of the water-soluble inorganic salt is preferably in a range of 0.01 part by mass or more but 1 part by mass or less, and more preferably in a range of 0.05 part by mass or more but 0.5 part by mass or less, with respect to 100 parts by mass of the solid content of the water absorbing resin. In other words, the water absorbing resin is preferably cross-linked by mixing the resin with an organic surface cross-linking agent and/or a water-soluble inorganic surface cross-linking agent containing a water-soluble inorganic salt (preferably, a persulfate) in a ratio of 0.01% by mass or more but 1.0% by mass or less, with respect to the water absorbing resin and then heating the mixture.

The method for mixing the surface cross-linking agent with the water absorbing resin is not particularly limited, and examples thereof include a mixing method in which the water absorbing resin is immersed in a hydrophilic organic solvent and mixed with a surface cross-linking agent dissolved, as necessary, in water and/or a hydrophilic organic solvent and a mixing method in which a surface cross-linking agent dissolved in water and/or a hydrophilic organic solvent is directly sprayed or added dropwise to the water absorbing resin.

After mixing the surface cross-linking agent with the water absorbing resin, generally, it is preferable that heating treatment be performed and the cross-linking reaction be allowed to proceed. The heating treatment temperature (heat medium temperature), although variable depending on the surface cross-linking agent to be used, is preferably 40° C. or higher but 250° C. or lower, and more preferably 150° C. or higher but 250° C. or lower. When the heating treatment temperature is lower than 40° C., there is a concern that absorbing properties such as the AAP (absorption capacity against a pressure) and SFC (physiological saline flow conductivity) is not sufficiently improved. When the heating treatment temperature is higher than 250° C., note that degradation of the water absorbing resin may occur and thus various physical properties may be lowered. The heating treatment time is preferably 1 minute or longer but 2 hours or shorter, and more preferably 5 minutes or longer but 1 hour or shorter.

Further, preferably, the surface cross-linking is performed in the presence of the α-hydroxy carboxylic acid (salt) described above. Accordingly, it is possible to obtain an effect of preventing the water absorbing resin from being colored.

(Additives Such as Polyvalent Metal Salt)

The method of producing a water absorbing resin according to the present invention preferably includes a step of adding a polyvalent metal salt to the water absorbing resin (preferably to the particle surface), particularly, in or after the surface cross-linking. The added amount of the polyvalent metal salt is preferably 0.001% by mass or more but 5% by mass or less, and more preferably 0.01% by mass or more but 1% by mass or less, with respect to the water absorbing resin.

Due to the addition of the polyvalent metal salt (preferably a water-soluble trivalent metal salt), the water absorbing resin according to the present invention exhibits improved SFC without significantly lowering the AAP of the water absorbing resin.

Specific examples of the polyvalent metal salt which can be used in the present invention include a sulfate, nitrate, carbonate, phosphate, organic acid salt, halide (chloride or the like) of a metal selected from Zn, Be, Mg, Ca, Sr, Al, Fe, Mn, Ti, Zr, Ce, Ru, Y, and Cr. Other examples are polyvalent metal salts described in Japanese Patent Application Laid-Open No. 2005-11317.

Further, among the polyvalent metal salts, water-soluble trivalent metal salts are most preferable. Specific examples of the water-soluble trivalent metal salts include aluminum chloride, polyaluminum chloride, aluminum sulfate, aluminum nitrate, aluminum potassium sulfate, aluminum sodium sulfate, potassium alum, ammonium alum, sodium alum, sodium aluminate, iron(III) chloride, cerium(III) chloride, ruthenium(III) chloride, yttrium(III) chloride, and chromium (III) chloride.

It is preferable to use these salts which contain crystal water in view of the solubility of absorbed liquid such as urine. Aluminum compounds are particularly preferable. Among them, aluminum chloride, polyaluminum chloride, aluminum sulfate, aluminum nitrate, bis aluminum potassium sulfate, bis aluminum sodium sulfate, potassium alum, ammonium alum, sodium alum, and sodium aluminate are preferable and aluminum sulfate is particularly preferable. An aqueous solution of aluminum sulfate (preferably, a solution of aluminum sulfate with a 90% or more concentration as based on saturation) can be used most preferably. Only one kind of these compounds may be used alone, or two or more kinds thereof may be used in combination.

Further, in the present invention, it is preferable to add a chelating agent, from a viewpoint of the color hue (prevention of coloration), prevention of deterioration, or the like of the water absorbing resin to be obtained. As the chelating agent, specifically, a compound and a used amount thereof disclosed in "[2] Chelating Agent" of International Publication No. WO 2011/040530 may be applied to the present invention.

Furthermore, in the present invention, an additive other than the above-described additive may also be added in order to provide various functions to the water absorbing resin. Specific examples of the additive include a surfactant, a compound having a phosphorus atom, an oxidizing agent, an organic reducing agent, water-insoluble inorganic particles, organic powder of metallic soap or the like, a deodorant, an antimicrobial agent, pulp, and thermoplastic fibers. Incidentally, a compound disclosed in International Publication No. WO 2005/075070 is applied to the present invention as the surfactant and a compound disclosed in "[5] Water-Insoluble Inorganic Particles" of International Publication No. WO 2011/040530 is applied to present invention as the water-insoluble inorganic particles. A used amount (added amount) of the additive is not particularly limited because it is decided as appropriate according to use application thereof, but is preferably 0.001% by mass or more but 3% by mass or less, and more preferably 0.01% by mass or more but 1% by mass or less, with respect to 100 parts by weight of water absorbing resin powder. Moreover, the additive can also be added in a step different from the above-described step.

The CRC of the water absorbing resin according to the present invention is generally 5 (g/g) or more, preferably 15 (g/g) or more, and still more preferably 25 (g/g) or more. The upper limit of the CRC is not particularly limited, and is preferably 70 (g/g) or less, more preferably 50 (g/g) or less, and still more preferably 40 (g/g) or less. When the CRC is less than 5 (g/g), in a case where the water absorbing resin is used for the water absorbing body, the absorption amount is too small and thus the water absorbing resin is not suitable for use of sanitary materials such as diapers. Meanwhile, when the CRC is more than 70 (g/g), in a case where the water absorbing resin is used for the water absorbing body, there is a concern that it is not possible to obtain a water absorbing resin having excellent speed of liquid absorption into the water absorbing body.

The AAP of the water absorbing resin according to the present invention is preferably 20 (g/g) or more, more preferably 22 (g/g) or more, still more preferably 23 (g/g) or more, and particularly preferably 24 (g/g) or more. The upper limit of the AAP is not particularly limited, and is preferably 30 (g/g) or less. When the AAP is less than 20 (g/g), in a case where the water absorbing resin is used for the water absorbing body, there is a concern that it is not possible to obtain a water absorbing resin having little amount of liquid squeezed out (so-called Re-Wet) when a pressure is applied to the water absorbing resin.

The SFC (physiological saline flow conductivity) of the water absorbing resin of the present invention is preferably $50(\times 10^{-7} \cdot cm^3 \cdot s \cdot g^{-1})$ or more, more preferably $60(\times 10^{-7} \cdot cm^3 \cdot s \cdot g^{-1})$ or more, still more preferably $70(\times 10^{-7} \cdot cm^3 \cdot s \cdot g^{-1})$ or more, and particularly preferably $80(\times 10^{-7} \cdot cm^3 \cdot s \cdot g^{-1})$ or more. The upper limit thereof is not particularly limited, and is preferably $3,000(\times 10^{-7} \cdot cm^3 \cdot s \cdot g^{-1})$ or less and more preferably $2,000(\times 10^{-7} \cdot cm^3 \cdot s \cdot g^{-1})$ or less. When the SFC is less than $50(\times 10^{-7} \cdot cm^3 \cdot s \cdot g^{-1})$, liquid permeability of body fluid such as urine or blood is low. Therefore, the water absorbing resin is not suitable for absorbing bodies of hygiene products such as disposable diapers. Meanwhile, when the SFC is more than $3,000(\times 10^{-7} \cdot cm^3 \cdot s \cdot g^{-1})$, there is a concern that body fluid such as urine or blood is not sufficiently absorbed and thus liquid leakage occurs. Therefore, the water absorbing resin is not suitable for absorbing bodies of hygiene products such as disposable diapers. Incidentally, the SFC can be controlled by a particle size, a surface cross-linking agent, a polyvalent metal salt, a cationic polymer, or the like.

In the water absorbing resin according to the present invention, an amount of the water soluble content (water soluble component) is preferably 0 to 35% by mass, more preferably 0 to 25% by mass, and still more preferably 0 to 15% by mass. When the amount of the water soluble content (water soluble component) is more than 35% by mass, gel strength may be weak and liquid permeability is poor. In addition, when the water absorbing resin is used for the water absorbing body, there is a concern that it is not possible to obtain a water absorbing resin having little amount of liquid squeezed out (so-called Re-Wet) when a pressure is applied to the water absorbing body.

The mass average particle size (D50) of the water absorbing resin according to the present invention is preferably 200 to 600 μm and more preferably 300 to 500 μm. When the mass average particle size (D50) of the water absorbing resin is not in a range of 200 to 600 μm, liquid permeability and diffusivity may be significantly lowered, or the absorption speed may be considerably lowered. In the case of using such a water absorbing resin, for example, as diapers, there is a concern that liquid leakage or the like occurs.

In the water absorbing resin according to the present invention, a logarithmic standard deviation ($\sigma\zeta$) of the particle size distribution is preferably 0.20 to 0.50 and more preferably 0.30 to 0.40. When the logarithmic standard deviation is not in the above range, there is a concern that the liquid permeability is lowered and thus a speed of liquid absorption into the water absorbing body is significantly deteriorated.

In the water absorbing resin according to the present invention, a proportion of particles having a size capable of passing through a sieve having a pore size of 150 µm and a proportion of particles having a size of 850 µm or more are preferably 0 to 5% by mass and more preferably 0 to 3% by mass, respectively. When the water absorbing resin, which includes particles having a size in a range of less than 150 µm in a small amount, is used, it is possible to suppress a powder dust amount of the water absorbing resin to be obtained. Therefore, it is possible to prevent problems relating to safety and hygiene caused by the scattering of fine particles included in the water absorbing resin when the water absorbing resin is produced, and to inhibit physical properties of the water absorbing resin to be obtained from being lowered. Meanwhile, in a case where the proportions are more than 5% by mass, powder dust is easily generated when the water absorbing resin is produced. Therefore, there is a concern that problems relating to safety and hygiene may occur or physical properties of the water absorbing body may be incurred.

[4] Absorbing Article

Figure 2:
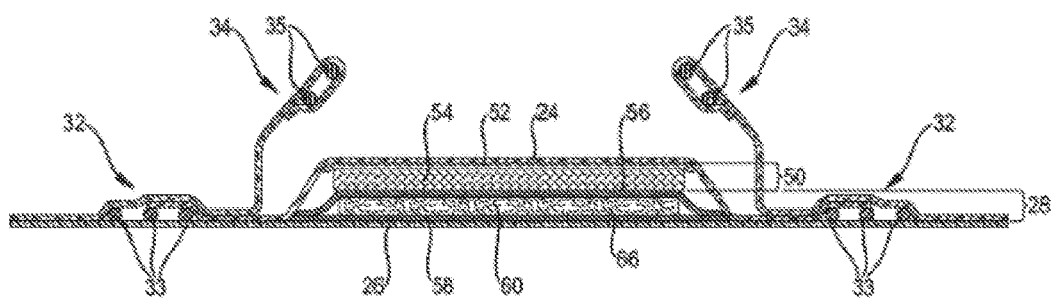
FIG. 2 is a transversal cross-section of the diaper of FIG. 1.

A typical absorbing article, in which the water absorbing resin, such as water absorbing resin particles, of the present invention can be used, is placed against or in proximity to the body of the wearer to absorb and contain the various exudates discharged from the body and is represented in FIGS. 1 and 2 in the form of a diaper 20.

The absorbing article of the present invention may be diposable and may be a disposable diaper or a disposable pant.

In more details, FIG. 1 is a plan view of an exemplary diaper 20, in a flat-out state, with portions of the diaper being cut-away to more clearly show the construction of the diaper 20. This diaper 20 is shown for illustration purpose only as the structure of the present invention may be comprised in a wide variety of diapers or other absorbing articles.

As shown in FIGS. 1 and 2, the absorbing article, here a diaper, can comprise a liquid pervious topsheet 24, a liquid impervious backsheet 26, an absorbing core 28 which is positioned between the topsheet 24 and the backsheet 26. The absorbing core 28 can absorb and contain liquid received by the absorbing article and may comprise absorbing materials 60, such as the water absorbing resin particles of the present invention 66 and/or cellulose fibers, as well as other absorbing and non-absorbing materials commonly used in absorbing articles (e.g. thermoplastic adhesives immobilizing the water absorbing resin particles). The absorbing material and non-absorbing material may be wrapped within a substrate (e.g. one or more nonwovens, tissues etc.) such as by an upper core cover layer 56 facing towards the topsheet and a lower cover layer 58 facing towards the backsheet. Such upper and lower core cover layers may be made of nonwovens, tissues or the like and may be attached to each other continuously or discontinuously, e.g. along their perimeter The absorbing core may comprise one or more substrate layer(s) (such as nonwoven webs or paper tissue), water absorbing resin, such as water absorbing resin particles, disposed on the one or more substrate layers, and a thermoplastic composition typically disposed on the water absorbing resin particles. Typically, the thermoplastic composition is a thermoplastic adhesive material. In one embodiment, the thermoplastic adhesive material forms a fibrous layer which is at least partially in contact with the water absorbing resin particles on the one or more substrate layers and partially in contact with the one or more substrate layers. Auxiliary adhesive might be deposited on the one or more substrate layers before application of the water absorbing resin particles for enhancing adhesion of the water absorbing resin particles and/or of the thermoplastic adhesive material to the respective substrate layer(s). The absorbent core may also include one or more cover layer(s) such that the water absorbing resin particles are comprised between the one or more substrate layer(s) and the one or more cover layer(s). The one or more substrate layer(s) and the cover layer(s) may comprise or consist of a nonwoven web. The absorbing core may further comprise odor control compounds.

The absorbing core may consist essentially of the one or more substrate layer(s), the water absorbing resin particles, the thermoplastic composition, optionally the auxiliary adhesive, optionally the cover layer(s), and optionally odor control compounds.

The absorbing core may also comprise a mixture of water absorbing resin particles and cellulose fibers (airfelt), which may be enwrapped within one or more substrate layers, such as nonwoven webs or paper tissue. Such absorbing cores may comprise from 30% to 95%, or from 50% to 95% of water absorbing resin, such as water absorbing resin particles, by weight of the absorbing material and may comprise from 5% to 70%, or from 5% to 50% of airfelt by weight of the absorbing material (for these percentages, any enwrapping substrate layers are not considered as absorbing material). Alternatively, the absorbing core may comprise less than 10% of airfelt by weight of the absorbent material (and may comprise at least 90% by weight of the water absorbing resin), or less than 5% of airfelt by weight of the absorbent material (and may comprise at least 95% by weight of the water absorbing resin), or may be free of airfelt and may comprise 100% of water absorbing resin, such as water absorbing resin particles, by weight of the absorbent material.

The absorbing articles of the invention, especially diapers and pants, may comprise an acquisition layer 52, a distribution layer 54, or combination of both (herein collectively referred to as acquisition-distribution system "ADS" 50). The function of the ADS 50 is typically to quickly acquire the fluid and distribute it to the absorbing core in an efficient manner. The ADS may comprise one, two or more layers. In the examples below, the ADS 50 comprises two layers: a distribution layer 54 and an acquisition layer 52 disposed between the absorbing core and the topsheet.

The ADS may be free of water absorbing resin. The prior art discloses many types of acquisition-distribution systems, see for example WO2000/59430, WO95/10996, U.S. Pat. No. 5,700,254, WO02/067809. However, the water absorbing resin, such as water absorbing resin particles, of the present invention may also be comprised by the ADS.

The function of a distribution layer 54 is to spread the insulting fluid liquid over a larger surface within the article so that the absorbing capacity of the absorbing core can be more efficiently used. Distribution layers may be made of a nonwoven material based on synthetic or cellulosic fibers and having a relatively low density. The distribution layer may typically have an average basis weight of from 30 to 400 g/m$^2$, in particular from 80 to 300 g/m$^2$.

The distribution layer may for example comprise at least 50%, or 60%, or 70%, or 80%, or 90% by weight of cross-linked cellulose fibers. The cross-linked cellulosic fibers may be crimped, twisted, or curled, or a combination thereof including crimped, twisted, and curled. The cross-linked cellulosic fibers provide higher resilience and therefore higher resistance to the first absorbing layer against the compression in the product packaging or in use conditions, e.g. under baby weight. This provides the core with a relatively high void volume, permeability and liquid absorption, and hence reduced leakage and improved dryness.

The distribution layer comprising cross-linked cellulose fibers, may comprise other fibers, but this layer may advantageously comprise at least 50%, or 60%, or 70%, or 80%, or 90% or even up to 100%, by weight of the layer, of cross-linked cellulose fibers. Examples of such mixed layer of cross-linked cellulose fibers may comprise 70% by weight of chemically cross-linked cellulose fibers, 10% by weight polyester (PET) fibers, and 20% by weight untreated pulp fibers. In another example, the layer of cross-linked cellulose fibers may comprise 70% by weight chemically cross-linked cellulose fibers, 20% by weight lyocell fibers, and 10% by weight PET fibers. In still another example, the layer may comprise 68% by weight chemically cross-linked cellulose fibers, 16% by weight untreated pulp fibers, and 16% by weight PET fibers.

The absorbing article 20 may further comprise an acquisition layer 52, whose function is to quickly acquire the fluid away from the topsheet so as to provide a good dryness for the wearer. The acquisition layer 52 is typically placed directly under the topsheet and above the distribution layer. The acquisition layer may typically be or comprise a nonwoven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). The binder may be present in the acquisition layer 52 in excess of 12%, 14% or 16% by weight, but may be present by not more than 30%, or not more than 25% by weight of the acquisition layer. SB latex is available under the trade name GENFLO™ 3160 (OMNOVA Solutions Inc.; Akron, Ohio).

A further acquisition layer may be used in addition to a first acquisition layer described above. For example, a tissue layer may be placed between the first acquisition layer and the distribution layer. The tissue may have enhanced capillarity distribution properties compared to the acquisition layer described above. The tissue and the first acquisition layer may be of the same size or may be of different size, for example, the tissue layer may extend further in the back of the absorbing article than the first acquisition layer. An example of hydrophilic tissue is a 13-15 gsm high wet strength made of cellulose fibers from supplier Havix.

The diaper may also comprise elasticized leg cuffs 32 and barrier leg cuffs 34, which provide improved containment of liquids and other body exudates especially in the area of the leg openings. Usually each leg cuffs 32 and barrier cuffs 34 will comprise one or more elastic string 33 and 35, represented in exaggerated form oin FIGS. 1 and 2. Moreover, the diaper 20 may comprise other features such as back ears 40, front ears 46 and/or barrier cuffs 34 attached to the topsheet and/or backsheet to form the composite diaper structure. The diaper may further comprise a fastening system, such as an adhesive fastening system or a mechanical fastening system (e.g. a hook and loop fastening system), which can comprise tape tabs 42, such as adhesive tape tabs or tape tabs comprising hook elements, cooperating with a landing zone 44 (e.g. a nonwoven web providing loops in a hook and loop fastening system). Further, the diaper may comprise other elements, such as a back elastic waist feature and a front elastic waist feature, side panels or a lotion application.

The diaper 20 as shown in FIGS. 1 and 2 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

EXAMPLES

Hereinafter, embodiments of water absorbent resins, which can be comprised by the absorbing articles the present invention, will be described in detail with reference to Examples. However, the present invention should not be construed in a limited way based on Examples. Further, various physical properties described in CLAIMS and EXAMPLES in this application are measured according to the following measuring method. Incidentally, unless particularly stated otherwise, the steps in Example are performed under substantially normal pressure (atmospheric pressure ±5%, further preferably 1% or less). Each step is performed without an intentional pressure change to increase or decrease the pressure throughout the step.

[Measuring Method of Various Physical Properties]

In a polypropylene vessel, a water absorbing resin (an amount in which 1.6 to 20 g of swollen gel can be obtained) was immersed in an excess (a weight equal to or more than 1,000 times as large as that of the water absorbing resin) of 0.9% by weight of aqueous solution of sodium chloride (a temperature of 21 to 25° C.) and was left to stand still for 48 hours. Thereafter, the aqueous solution was removed in the polypropylene vessel, and 0.9% by weight aqueous solution of sodium chloride was added again thereto, followed by being left to stand still for 48 hours. After that, the aqueous solution was removed in the polypropylene vessel, and 0.9% by weight aqueous solution of sodium chloride was added again thereto, followed by being left to stand still for 48 hours. Therefore, a dispersion liquid of a gel in an equilibrium swollen state (hereinafter, referred to as an equilibrium swollen gel) was obtained.

The equilibrium swollen gel thus obtained was weighed in a range of 1.6 to 2.4 g (mass W1) by 0.1 mg unit and the equilibrium swelling capacity of the following formula (a ratio (g/g) of water absorbing resin solid content W (g) and an amount (g) of 0.9% by weight aqueous solution of sodium chloride absorbed by the water absorbing resin) was calculated from the mass (W1) of the equilibrium swollen gel and the polymer solid content W of the equilibrium swollen gel.

Equilibrium swelling capacity (g/g) with respect to 0.9% by weight of brine=W1/W−1

In this regard, the mass W1 of the equilibrium swollen gel and the polymer solid content W in the formula are obtained in the following manner.

(Measuring Method of Mass W1 of Equilibrium Swollen Gel)

The total amount of the dispersion liquid of the equilibrium swollen gel obtained above was put in a resin cylinder (inner diameter: 6 cm, height: 5 cm), on the lower bottom of which has a wire mesh with a pore size of 36 μm (corresponding to 400 mesh), for AAP measurement described in ERT442.2-02, and further draining was performed by natural filtration for 5 minutes. After the filtration, further, in a case where the gel was a particulate gel, the gel was uniformly put in the cylinder by using a spatula without compression to be a planar state such that the entire bottom surface of the cylinder was covered; meanwhile, in a case where the gel was a clumped gel with which the entire bottom surface of the cylinder cannot be covered, the gel was put in the cylinder such that the contact lower surface area of the clumped gel with respect to the cylinder bottom surface became maximum. Thereafter, for further draining, the cylinder was placed on five-sheet-stacked filter paper (Advantec No. 2, diameter: 150 mm) and then left to stand still for 5 minutes in the environment at room temperature of 15 to 30° C. and a humidity of 30 to 90%. After that, the cylinder was placed newly on five-sheet-stacked filter paper (Advantec No. 2, diameter: 150 mm), left to stand still for 5 minutes in the environment at room temperature of 15 to 30° C. and a humidity of 30 to 90%, and then the drained gel was weighed in a predetermined weight (mass W1).

(Measuring Method of Polymer Solid Content W of Equilibrium Swollen Gel)

The polymer solid content of the equilibrium swollen gel (mass W1) was obtained by drying loss. At this time, first, the solid content of NaCl in the gel was removed by the following manner. That is, the gel thus weighed (mass W1) was transferred into a polypropylene vessel (manufactured by TGK) having a capacity of 250 ml and immersed in 200 ml of pure water (a temperature of 21 to 25° C.), and the vessel was covered with a lid and left to stand still for 48 hours. Thereafter, liquid in the polypropylene vessel was removed and 200 ml of pure water (a temperature of 21 to 25° C.) was added again thereto. The vessel was covered with a lid and left to stand still for 48 hours. After that, liquid in the polypropylene vessel was removed and 200 ml of pure water (a temperature of 21 to 25° C.) was added again thereto. The vessel was covered with a lid and left to stand still for 48 hours.

The pure water-swollen gel obtained by removing NaCl was placed on an aluminum cup (mass W0) having a bottom surface diameter of about 5 cm. In a case where a major diameter of the obtained pure water-swollen gel was more than 3 mm, the pure water-swollen gel was cut by scissors to have a major diameter of about 3 mm. The aluminum cup was left to stand still for 4 hours in a windless drying machine (ADVANTEC DRV320DA) having a temperature of 180° C. for drying. After the drying, the total (W2) of the mass of the aluminum cup and the mass of the cross-linked polymer (solid content) was measured to obtain the polymer solid content W (=W2−W0) in the equilibrium swollen gel (W1).

<Elastic Modulus of Swollen Gel>

(Sample Preparation)

The gel that had reached the equilibrium swollen state in the 0.9% by weight of aqueous solution of sodium chloride was transferred to a stainless steel vat (20 cm×12.5 cm×7 cm). The gel was cut out into a cylindrical shape having a diameter of 25 mm by using a steel punch (POSK25, high-class belt punch, 25 mm, manufactured by Trusco Nakayama Corporation). The elastic modulus of the gel was measured by a shear test according to the following conditions.

(Elastic Modulus Measuring Condition)

Measuring instrument: MCR 301 (manufactured by Anton Paar GmbH)

Jig: Aluminum plate having a diameter of 25 mm

Strain: 0.01%

Frequency: 1 Hz

Measuring method: First, the gel was sheared according to the above conditions under a load of 0.34 N and a storage elastic modulus was measured every 10 seconds for 5 minutes. An average value of the storage elastic modulus at 120 seconds to 300 seconds after starting the measurement was set to an elastic modulus ($G_0$) under a load of 0.34 N. Thereafter, the load applied to the gel was increased by 0.68 N in a stepwise manner (that is, the load was set to (0.34+0.68×n) N (n=1, 2, 3, . . . m−1, m, m+1, . . . )), and the elastic modulus ($G_n$) under each load was measured. At the time point at which both of a difference between a measurement value ($G_m$) of the elastic modulus under a load of (0.34+0.68×m) N and a measurement value ($G_{m-1}$) of the elastic modulus under the load immediate before the above load, and a difference between the measurement value ($G_m$) and a measurement value ($G_{m+1}$) of the elastic modulus under the load immediate after the above load became 5% or less, $G_m$ was set to the elastic modulus of the gel.

<Weight Average Molecular Weight after Hydrolysis Treatment>

(Sample Preparation)

The gel that had reached the equilibrium swollen state in 0.9% by weight of aqueous solution of sodium chloride was weighed in an amount of (50× physiological saline equilibrium swelling capacity) mg and put in a polypropylene vessel (manufactured by TGK) having a capacity of 120 ml. 10 g of 0.1 mol/l aqueous solution of sodium hydroxide was added thereto. The vessel was covered with a lid and left to stand still for 3 weeks in a windless drying machine (ADVANTEC DRV320DA) having a temperature of 80° C. After 3 weeks, the gel was hydrolyzed to be in a solution state.

The solution thus obtained was diluted with the following eluent by four times, and allowed to pass through a filter (manufactured by GL Sciences, Inc., GL Chromatodisk, aqueous system 25A, and pore size of 0.2 μm). The GPC measurement of this solution was performed according to the following conditions.

(GPC Measuring Conditions)

The measurement was performed using TDA 302 (registered trademark) manufactured by Viscotech Co., Ltd. The device is configured to include a size exclusion chromatography, a refractive index detector, a light scattering detector, and a capillary viscometer. The measuring devices and measuring conditions were as follows.

Pump-autosampler: GPC max manufactured by Viscotech Co., Ltd.

Guard column: OHpak SB-G (manufactured by SHOWA DENKO K. K.)

Column: Two OHpak SB-806MHQs (manufactured by SHOWA DENKO K. K.) connected in series for use Detector: TDA 302 manufactured by Viscotech Co., Ltd. (a temperature inside the system was kept at 30° C.)

Eluent: Aqueous solution (pH 6.35 to 6.38) including 60 mM of sodium dihydrogen phosphate dihydrate, 20 mM of disodium hydrogenphosphate dodecahydrate, and 400 ppm of sodium azide Flow rate: 0.5 ml/min Injection amount: 100 μl As pure water to be used in this measurement, pure water in which impurities were sufficiently removed was used. Further, the measurement was performed in a state where a sufficient amount of the solvent was allowed to flow into the device and the base line of the detector was stable. In particular, the measurement was performed in a state where there was no noise peak in the light scattering detector.

The device calibration was performed by using polyoxyethylene glycol (weight average molecular weight (Mw) of 22,396, molecular weight distribution (Mw/Mn=1.0), differential refractive index (dn/dc)=0.132, and solvent refractive index of 1.33) as a reference sample. Further, the differential refractive index (dn/dc) of a polymer subjected to the analysis was set to 0.132 and the solvent refractive index thereof was set to 1.33 in the measurement.

Data on the refractive index, light scattering intensity, and viscosity was collected and analyzed with use of Viscotek OmniSEC 3.1 (registered trademark) software. The weight average molecular weight (Mw), the number average molecular weight (Mn), the molecular weight distribution (Mw/Mn), and the inherent viscosity (IV) were calculated based on data obtained from the refractive index (RI), light scattering intensity (angle of 7°) LALS and viscometer (DP). Incidentally, in this specification, the inherent viscosity (IV) is synonymous with the intrinsic viscosity (IV).

<Weight Average Molecular Weights of Star-Shaped Polymers (1-$N_3$) to (4-$N_3$)>

The GPC measurement was performed according to the following devices and conditions.

Measuring instrument: HLC-8120 (manufactured by TOSOH CORPORATION)

Column: Two of G5000HXL (manufactured by TOSOH CORPORATION) and GMHXL-L (manufactured by TOSOH CORPORATION) connected in series for use Eluent: Tetrahydrofuran Calibration curve reference material: Polystyrene Measuring method: A measurement object was dissolved in an eluent to have a solid content of 0.3% by mass, and the resulting solution was filtered with a filter before being subjected to measurement. The measurement was performed in a state where a sufficient amount of the solvent was allowed to flow into the device and the base line of the detector was stable.

Example 1

Synthesis of Four-Arm Star-Shaped Core

A four-arm star-shaped core having a chemical structure represented by the following Chemical Formula A was synthesized by the method described in Scheme 1 (Page 14601) of prior art document (J. Am. Chem. Soc., 2006, 128, 14599-14605).

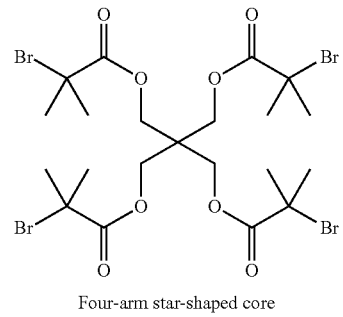

[Chemical Formula A]

Four-arm star-shaped core (Synthesis of Four-Arm Star-Shaped Polymer (1-Br))

In a 50 ml recovery flask having a stirrer therein and filled with nitrogen, 80 mg of copper (I) bromide and 6 mg of copper (II) bromide were dissolved in 2.0 g of acetone and 14.1 g of tert-butyl acrylate. 107 mg of pentamethyldiethylenetriamine was added thereto and a mixture was stirred for 5 minutes at room temperature. Thereafter, 0.2 g of the four-arm star-shaped core synthesized above was added to the mixture to prepare a reaction solution. The reaction solution was stirred in an oil bath having a temperature of 50° C. for 1.5 hours while heating. The obtained solution was dried under reduced pressure at room temperature and 1 mm Hg for 5 hours to obtain a crude product of a four-arm star-shaped polymer (1-Br) having a chemical structure represented by the following Chemical Formula B. A solution obtained by dissolving the crude product in 100 ml of diethyl ether was transferred to a separation funnel, and 100 ml of pure water was added thereto, followed by being mixed by shaking. The recovered organic layer was transferred to the separation funnel, and 100 ml of pure water was added thereto again, followed by being mixed by shaking. The obtained organic layer was dried under reduced pressure at room temperature and 1 mmHg for 5 hours to obtain a solid four-arm star-shaped polymer (1-Br). The chemical structure of the obtained product was confirmed by proton NMR measurement using deuterated chloroform as a solvent. As a characteristic peak, a peak appearing at a chemical shift position of 4.1 ppm, which is derived from hydrogen on carbon having a bromine functional group, is exemplified.

[Chemical Formula B]

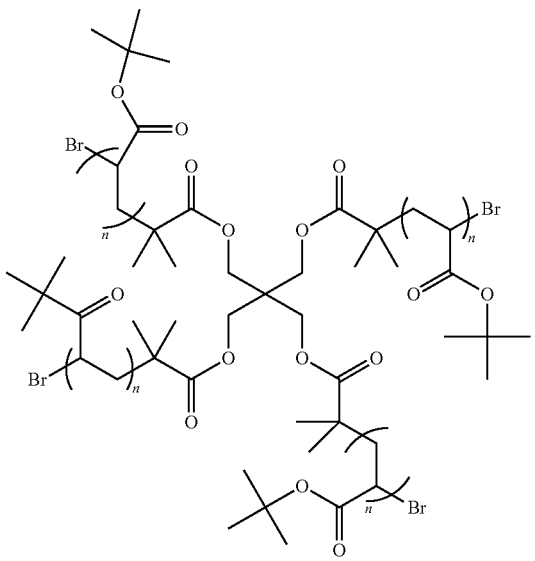

Four-arm star-shaped polymer (1-Br)

n = 20

(Synthesis of Four-Arm Star-Shaped Polymer (1-$N_3$))

In a 50 ml recovery flask having a stirrer therein and filled with nitrogen, 2.0 g of the four-arm star-shaped polymer (1-Br) synthesized above and 156 mg of sodium azide were dissolved in 10 ml of dimethylformamide to prepare a reaction solution. The reaction solution was stirred at room temperature for 18 hours and then dried under reduced pressure in a hot-water bath having a temperature of 50° C. at 1 mmHg for 5 hours to obtain a crude product of a four-arm star-shaped polymer (1-$N_3$) having a chemical structure represented by the following Chemical Formula C. A solution obtained by dissolving the crude product in 100 ml of diethyl ether was transferred to a separation funnel, and 100 ml of pure water was added thereto, followed by being mixed by shaking. The recovered organic layer was transferred to the separation funnel, and 100 ml of pure water was added thereto again, followed by being mixed by shaking. The obtained organic layer was dried under reduced pressure at room temperature and 1 mmHg for 5 hours to obtain a solid four-arm star-shaped polymer (1-$N_3$). The chemical structure of the obtained product was confirmed by proton NMR measurement using deuterated chloroform as a solvent. As a characteristic peak, a peak appearing at a chemical shift position of 3.7 ppm, which is derived from hydrogen on carbon having an azido functional group, is exemplified.

The weight average molecular weight Mw of the four-arm star-shaped polymer (1-$N_3$) thus obtained was 12,550 and the molecular weight distribution Mw/Mn thereof was 1.15.

[Chemical Formula C]

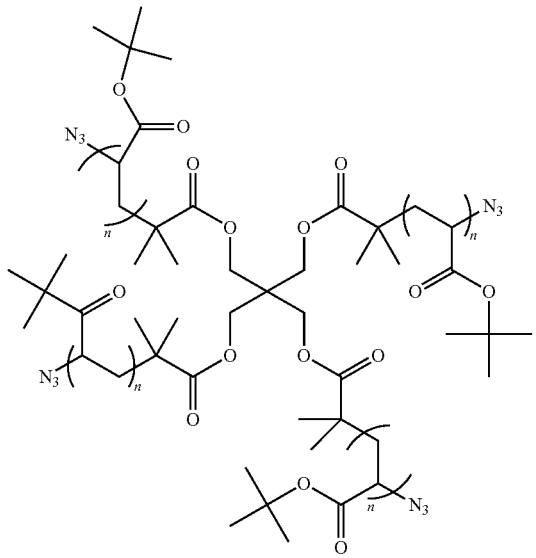

Four-arm star-shaped polymer (1-$N_3$)
n = 20

(Synthesis of Dialkyne)

Dialkyne having a chemical structure represented by the following Chemical Formula D was obtained by the method described in prior art document (J. Am. Chen. Soc. 2007, 129, 12916-12917). Specifically, as described in Supporting Information (S2) of J. Am. Chen. Soc. 2007, 129, 12916-12917, a tetrahydrofuran solution of 2-(propane-2-ynyl) dimethyl malonate (1.0 mmol) was treated with NaH (1.5 mmol) at 0° C. and stirring was continued for 30 minutes at room temperature. Thereafter, (3-bromopropane-1-ynyl) trimethylsilane (1.5 mmol) was added as an alkylating agent and then the reaction was allowed to proceed.

[Chemical Formula D]

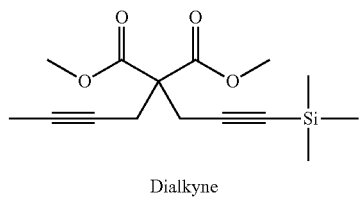

Dialkyne (Synthesis of Four-Arm Star-Shaped Polymer (1-Si Alkyne))

In a 50 ml recovery flask having a stirrer therein and filled with nitrogen, 1.0 g of the four-arm star-shaped polymer (1-$N_3$) synthesized above, 134.6 mg of dialkyne synthesized above, and 57.4 mg of copper (I) bromide were dissolved in 10 ml of dimethylformamide. 76.8 mg of pentamethyldiethylenetriamine was added thereto to prepare a reaction solution. The reaction solution was stirred for 18 hours at room temperature and then dried under reduced pressure in hot-water bath having a temperature of 50° C. at 1 mmHg for 5 hours to obtain a crude product of a four-arm star-shaped polymer (1-Si alkyne) having a chemical structure represented by the following Chemical Formula E. A solution obtained by dissolving the crude product in 100 ml of diethyl ether was transferred to a separation funnel, and 100 ml of pure water was added thereto, followed by being mixed by shaking. The recovered organic layer was transferred to the separation funnel, and 100 ml of pure water was added thereto again, followed by being mixed by shaking. The obtained organic layer was dried under reduced pressure at room temperature and 1 mmHg for 5 hours and the generated solid product was washed with 50 ml of hexane 3 times to obtain a solid four-arm star-shaped polymer (1-Si alkyne). The chemical structure of the obtained product was confirmed by proton NMR measurement using deuterated chloroform as a solvent. As characteristic peaks, a peak derived from hydrogen on a 1,2,3-triazole ring appeared at a chemical shift position of 7.5 ppm, a peak derived from hydrogen on carbon having a 1,2,3-triazole ring appeared at a chemical shift position of 5.2 ppm, and a peak derived from hydrogen of a trimethylsilyl group appeared at a chemical shift position of 0.1 ppm are exemplified.

[Chemical Formula E]

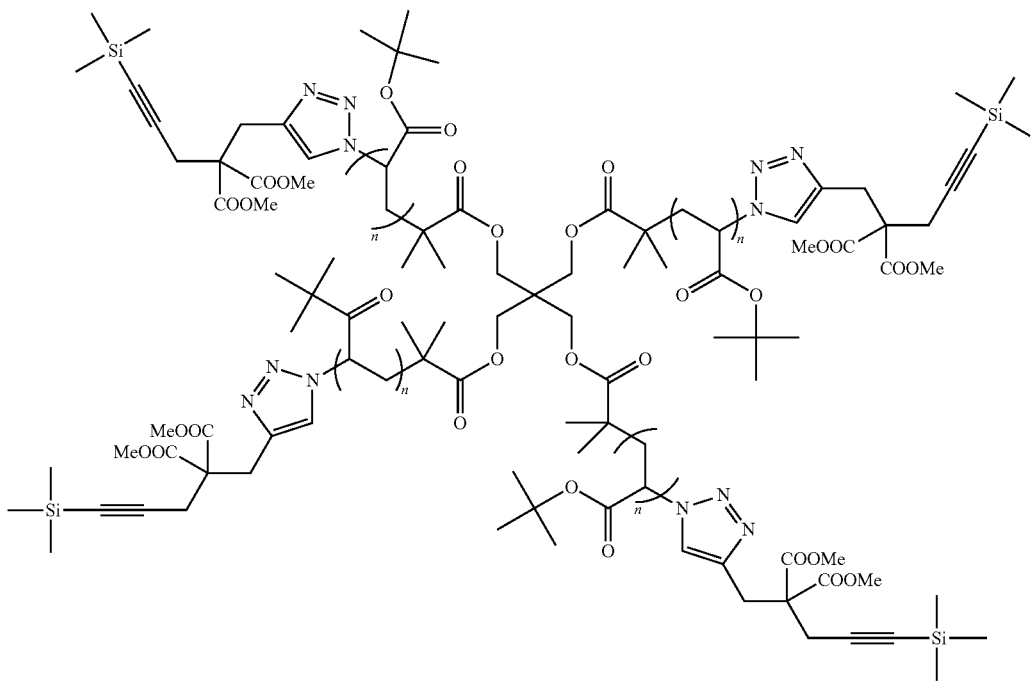

Four-arm star-shaped polymer (1-Si alkyne)

n = 20

(Synthesis of Four-Arm Star-Shaped Polymer (1-H Alkyne))

In a 50 ml recovery flask having a stirrer therein and filled with nitrogen, 1.0 g of the four-arm star-shaped polymer (1-Si alkyne) synthesized above was dissolved in 10 ml of tetrahydrofuran and cooled to 0° C. 1.4 ml of 1 mol/L tetrahydrofuran solution of tetrabutylammonium fluoride was added thereto to prepare a reaction solution. The reaction solution was returned to room temperature, stirred for 18 hours, and dried under reduced pressure at room temperature and 1 mmHg for 5 hours to obtain a crude product of a four-arm star-shaped polymer (1-H alkyne). A solution obtained by dissolving the crude product in 100 ml of diethyl ether was transferred to a separation funnel, and 100 ml of pure water was added thereto, followed by being mixed by shaking. The recovered organic layer was transferred to the separation funnel, and 100 ml of pure water was added thereto again, followed by being mixed by shaking. The obtained organic layer was dried under reduced pressure at room temperature and 1 mmHg for 5 hours and the generated solid product was washed with 50 ml of hexane 3 times to obtain a solid four-arm star-shaped polymer (1-H alkyne). The chemical structure of the obtained product was confirmed by proton NMR measurement using deuterated chloroform as a solvent. As is the case in the above-described 1-Si alkyne, as characteristic peaks, a peak derived from hydrogen on a 1,2,3-triazole ring appeared at a chemical shift position of 7.5 ppm and a peak derived from hydrogen on carbon having a 1,2,3-triazole ring appeared at a chemical shift position of 5.2 ppm. On the other hand, from the fact that a peak did not appear at a chemical shift position of 0.1 ppm, it was confirmed that deprotection reaction of a trimethylsilyl group has been performed.

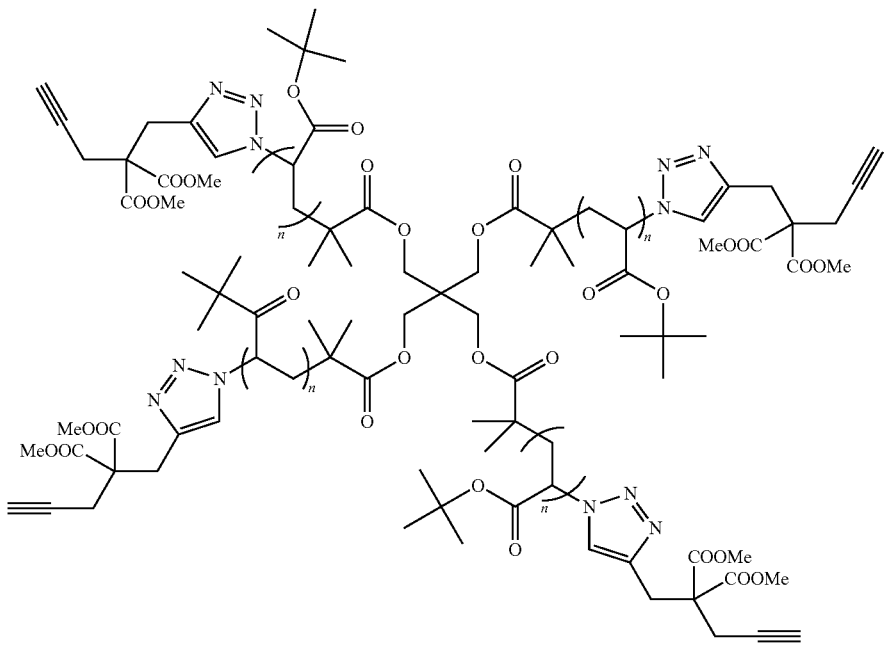

Four-arm star-shaped polymer (1-H alkyne)

n = 20

(Synthesis of Poly(tert-Butyl Acrylate) Cross-Linked Body (1-tBA Gel))

In a glass vial having a stirrer therein and filled with nitrogen, 92.0 mg of the four-arm star-shaped polymer (1-$N_3$) synthesized above and 100.0 mg of the four-arm star-shaped polymer (1-H alkyne) synthesized above were dissolved in 533.0 μl of acetone and cooled to 0° C. A solution obtained by dissolving 5.7 mg of copper (I) bromide and 7.7 mg of pentamethyldiethylenetriamine in 133.0 μl of methanol using another glass vial was added thereto to prepare a reaction solution. The reaction solution was stirred for 30 seconds and then the stirrer was taken out from the vial, followed by being left to stand still at room temperature. As a result, the reaction solution was hardened after about 30 minutes so as to become a gel. Thereafter, the glass vial was left to stand still at room temperature for 18 hours. The generated gel was taken out from the glass vial. In a 50 ml glass beaker, the obtained gel was immersed in 30 ml of acetone. The glass beaker was placed on a shaker and shaken for 24 hours at a speed of 60 revolutions per minute, and the remaining copper was washed off. The obtained acetone-swollen gel was taken out from the glass beaker and left to stand still for 24 hours at room temperature in air for drying. As a result, a cylindrical poly(tert-butyl acrylate) cross-linked body (1-tBA gel) having a chemical structure represented by the following Chemical Formula G was obtained.

[Chemical Formula G]

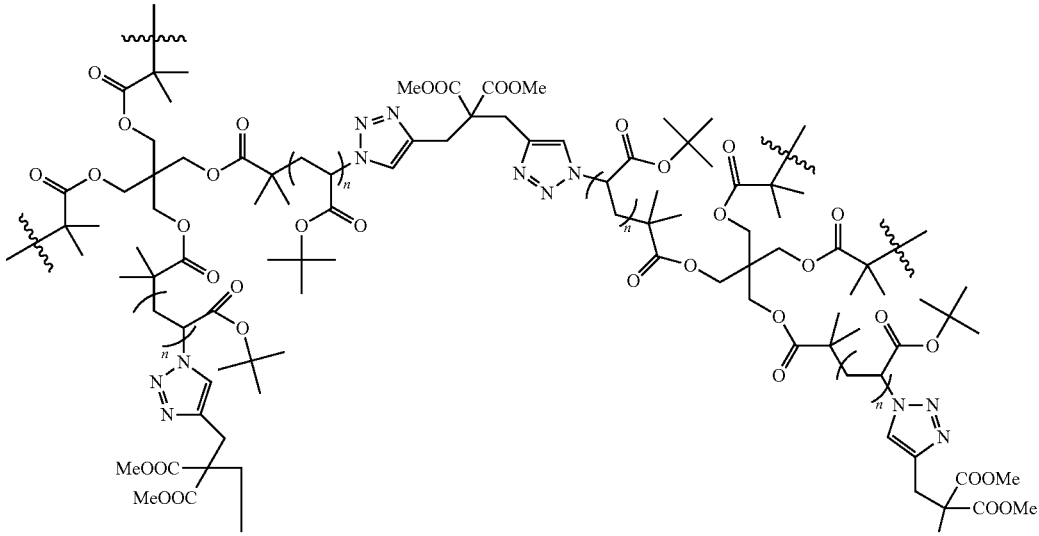

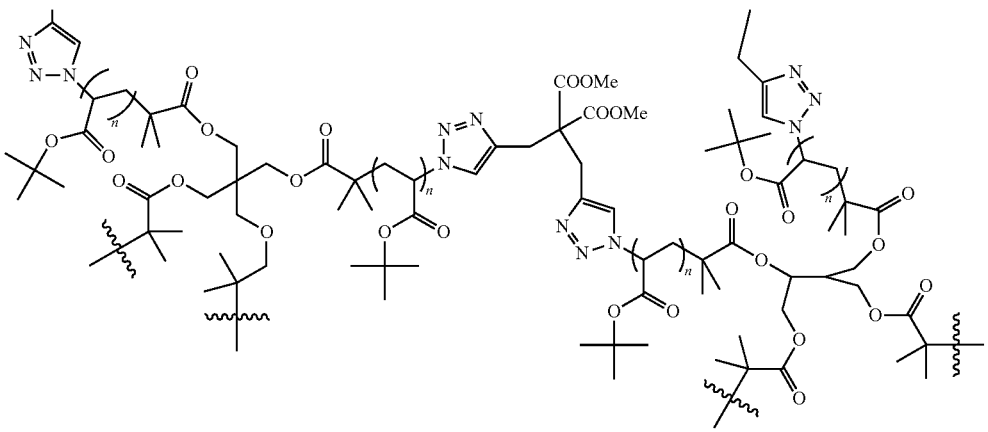

Poly(tert-butyl acrylate) cross-linked body (1-tBA gel)

n = 20

(Synthesis of Water-Swollen Gel (1-AA Gel) of Polyacrylic Acid Cross-Linked Body)

The poly(tert-butyl acrylate) cross-linked body (1-tBA gel) synthesized above was transferred into a 50 ml glass beaker and immersed in a mixture solution of 12 ml of dichloromethane and 3 ml of trifluoroacetic acid. The glass beaker was placed on a shaker and shaken for 24 hours at a speed of 60 revolutions per minute. At this time, the cross-linked body absorbed the mixture solution once to be swollen. However, since the deprotection reaction of a tert-butyl group gradually proceeded due to trifluoroacetic acid, the mixture solution was discharged again such that the cross-linked body was contracted. This polyacrylic acid cross-linked body generated by the deprotection reaction of a tert-butyl group was taken out from the glass beaker and immersed in 30 ml of pure water using another 50 ml glass beaker. The glass beaker was placed on a shaker and shaken for 18 hours at a speed of 60 revolutions per minute, and the remaining trifluoroacetic acid was washed off. As a result, a cylindrical water-swollen gel (1-AA gel) of polyacrylic acid cross-linked body having a chemical structure represented by the following Chemical Formula H was obtained.

[Chemical Formula H]

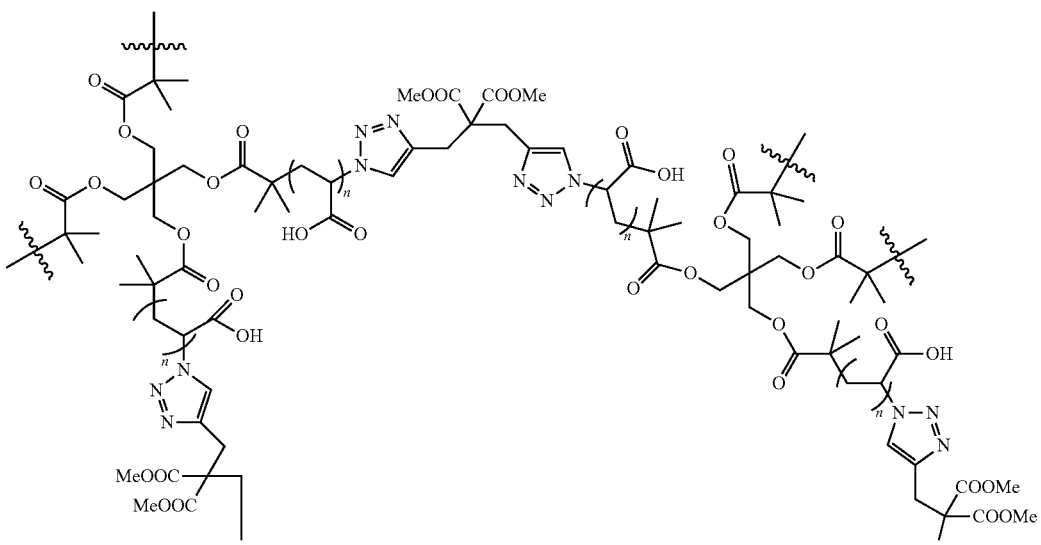

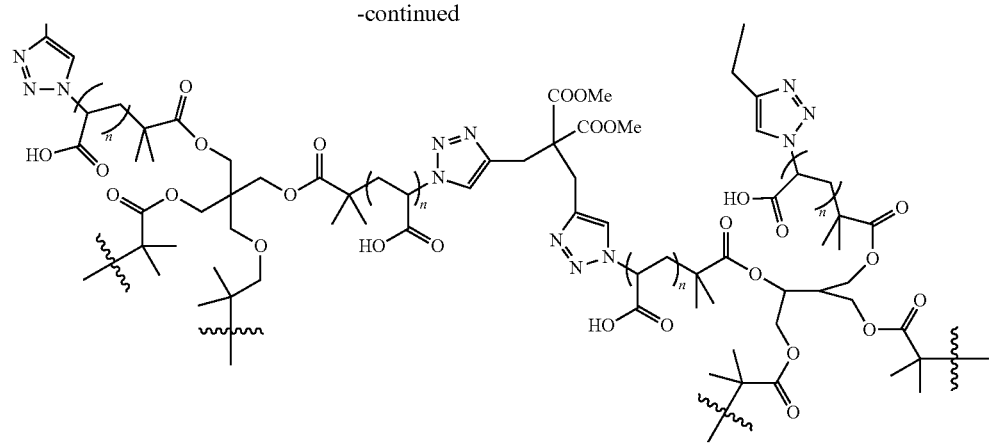

Water-swollen gel of polyacrylic acid cross-linked body (1-AA gel)

n = 20

(Synthesis of Swollen Gel, which was Swollen to Equilibrium in 0.9% by Weight of Aqueous Solution of Sodium Chloride, of Cross-Linked Body of Partially-Neutralized Polyacrylic Acid (Water Absorbing Resin 1))

In a 120 ml polypropylene vessel (manufactured by TGK), 94.5 mg of sodium hydrogen carbonate was dissolved in 30 ml of 0.9% by weight aqueous solution of sodium chloride and the water-swollen gel (1-AA gel) of polyacrylic acid cross-linked body synthesized above was immersed in the above solution, followed by being left to stand still for 72 hours. The obtained swollen gel (water absorbing resin 1) of the cross-linked body of partially-neutralized polyacrylic acid was transferred into a 250 ml polypropylene vessel and immersed in 200 ml of 0.9% by weight aqueous solution of sodium chloride, followed by being left to stand still for 48 hours. Thereafter, the aqueous solution was removed in the polypropylene vessel and 200 ml of 0.9% by weight aqueous solution of sodium chloride was added again thereto, followed by being left to stand still for 48 hours. After that, the aqueous solution was removed in the polypropylene vessel and 200 ml of 0.9% by weight aqueous solution of sodium chloride was added again thereto, followed by being left to stand still for 48 hours. In this way, a swollen gel, which was swollen to equilibrium in 0.9% by weight of aqueous solution of sodium chloride, of the cross-linked body of partially-neutralized polyacrylic acid (water absorbing resin 1) was obtained. The swollen gel (water absorbing resin 1) has a chemical structure represented by the following Chemical Formula I.

[Chemical Formula I]

Swollen gel, which is swollen to equilibrium in 0.9% by weight of aqueous solution of sodium chloride, of a cross-linked body of partially-neutralized polyacrylic acid (water absorbing resin 1)

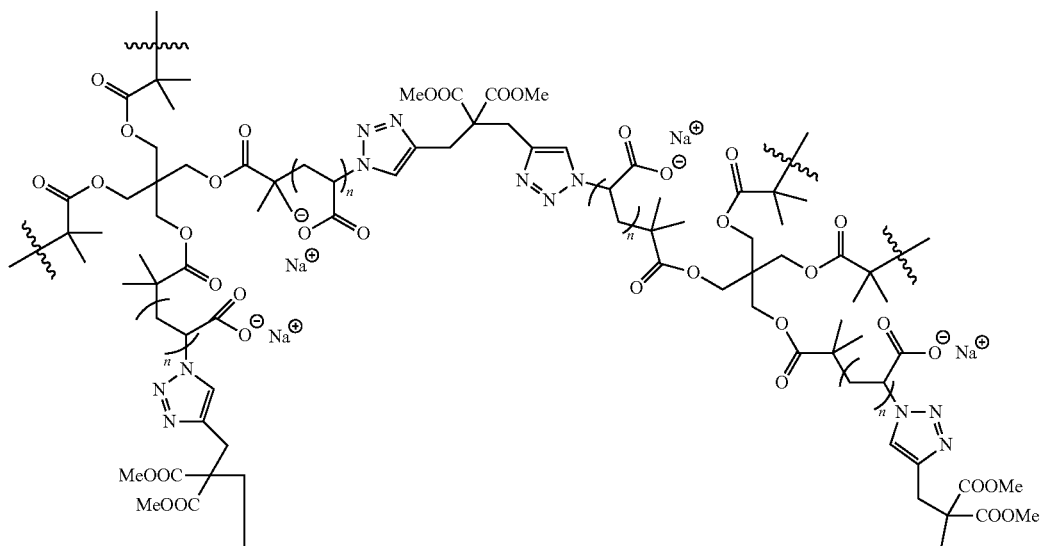

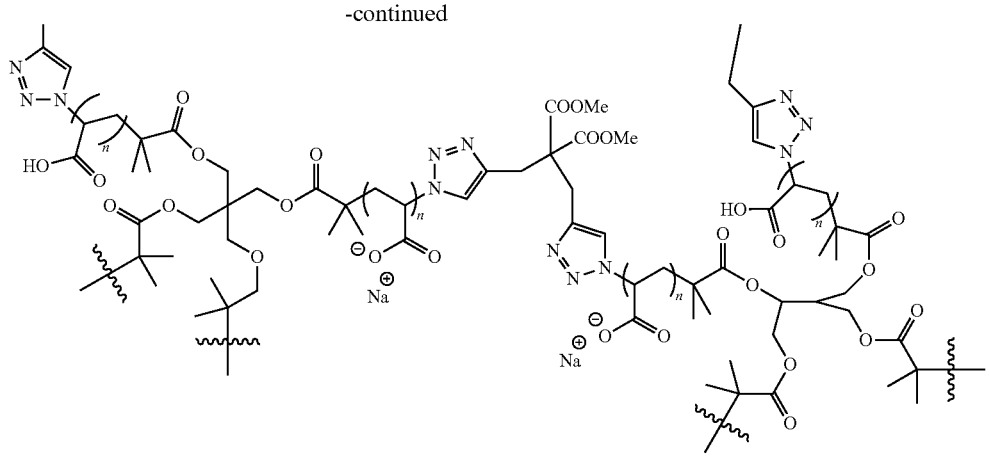

n = 20

Figure 3:
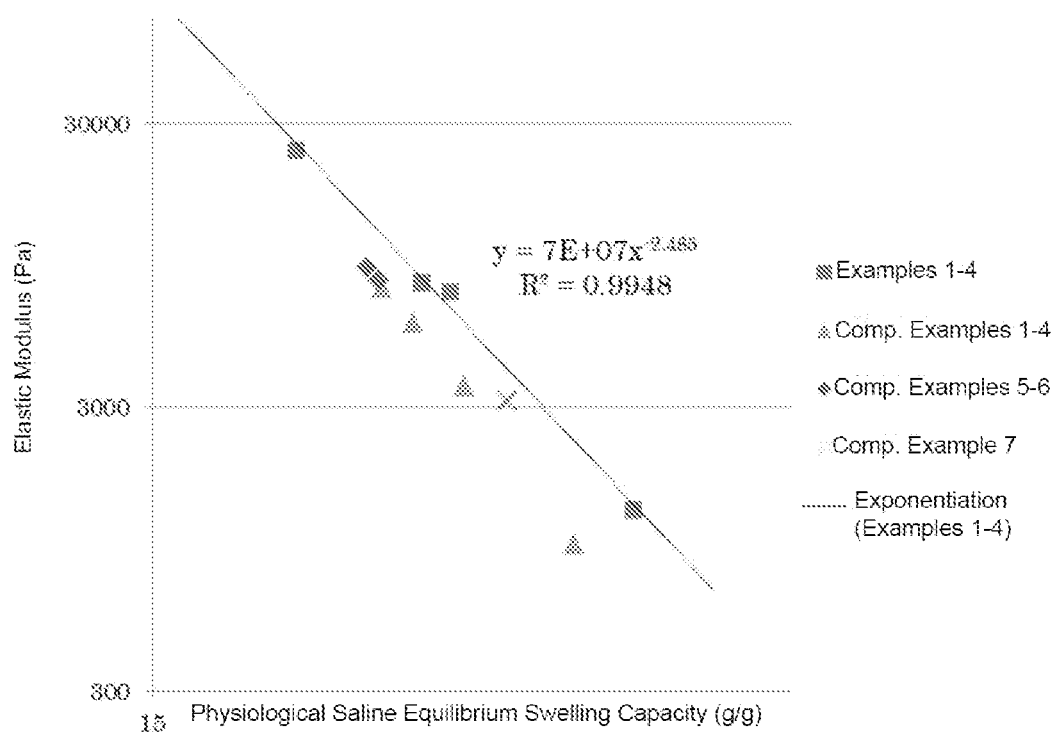
FIG. 3 is a graph obtained by plotting a logarithmic value of the equilibrium swelling capacity measured in each water absorbing resin produced in Examples and Comparative Examples in a horizontal axis and a logarithmic value of an elastic modulus (Pa) in a vertical axis (the origin is an equilibrium swelling capacity of 15 g/g and an elastic modulus of 300 Pa).

The equilibrium swelling capacity of the swollen gel, which was swollen to equilibrium in 0.9% by weight of aqueous solution of sodium chloride, of the cross-linked body of partially-neutralized polyacrylic acid (water absorbing resin 1) was 24.8 g/g and the elastic modulus thereof was 24,276 Pa. Further, the weight average molecular weight Mw after hydrolysis was 7,355 and the molecular weight distribution Mw/Mn was 1.06. These results are presented in the following Table 1. Furthermore, FIG. 3 illustrates a graph obtained by plotting logarithmic values of the equilibrium swelling capacity in a horizontal axis and logarithmic values of the elastic modulus (Pa) in a vertical axis (the origin is an equilibrium swelling capacity of 15 g/g and an elastic modulus of 300 Pa) (the same is true of the following Examples and Comparative Examples).

Example 2

Synthesis of Four-Arm Star-Shaped Polymer (2-Br)

A solid four-arm star-shaped polymer (2-Br) having a chemical structure (n=30) in the above Chemical Formula B was obtained in the same manner as in "Synthesis of Four-Arm Star-Shaped Polymer (1-Br)" in Example 1 except that an amount of tert-butyl acrylate was set to 17.6 g and the reaction time was set to 2 hours.

(Synthesis of Four-Arm Star-Shaped Polymer (2-$N_3$))

A solid four-arm star-shaped polymer (2-$N_3$) having a chemical structure (n=30) in the above Chemical Formula C was obtained in the same manner as in "Synthesis of Four-Arm Star-Shaped Polymer (1-$N_3$)" in Example 1 except that the four-arm star-shaped polymer (2-Br) synthesized above was used instead of the four-arm star-shaped polymer (1-Br) and an amount of sodium azide (Na$N_3$) was set to 110 mg.

The weight average molecular weight Mw of the four-arm star-shaped polymer (2-$N_3$) thus obtained was 17,029 and the molecular weight distribution Mw/Mn thereof was 1.11.

(Synthesis of Four-Arm Star-Shaped Polymer (2-Si Alkyne))

A solid four-arm star-shaped polymer (2-Si alkyne) having a chemical structure (n=30) in the above Chemical Formula E was obtained in the same manner as in "Synthesis of Four-Arm Star-Shaped Polymer (1-Si alkyne)" in Example 1 except that the four-arm star-shaped polymer (2-$N_3$) synthesized above was used instead of the four-arm star-shaped polymer (1-$N_3$), an amount of dialkyne was set to 89.7 mg, an amount of copper (I) bromide was set to 38.1 mg, and an amount of pentamethyldiethylenetriamine was set to 51.2 mg.

(Synthesis of Four-Arm Star-Shaped Polymer (2-H Alkyne))

A solid four-arm star-shaped polymer (2-H alkyne) having a chemical structure (n=30) in the above Chemical Formula F was obtained in the same manner as in "Synthesis of Four-Arm Star-Shaped Polymer (1-H alkyne)" in Example 1 except that the four-arm star-shaped polymer (2-Si alkyne) synthesized above was used instead of the four-arm star-shaped polymer (1-Si alkyne) and an amount of 1 mol/L tetrahydrofuran solution of tetrabutylammonium fluoride was set to 1.0 ml.

(Synthesis of Poly(tert-Butyl Acrylate) Cross-Linked Body (2-tBA Gel))

A cylindrical poly(tert-butyl acrylate) cross-linked body (2-tBA gel) having a chemical structure (n=30) in the above Chemical Formula G was obtained in the same manner as in "Synthesis of Poly(tert-Butyl Acrylate) Cross-Linked Body (1-tBA Gel)" in Example 1 except that 94.8 mg of the four-arm star-shaped polymer (2-$N_3$) synthesized above was used instead of 92.0 mg of the four-arm star-shaped polymer (1-$N_3$), the four-arm star-shaped polymer (2-H alkyne) synthesized above was used instead of the four-arm star-shaped polymer (1-H alkyne), an amount of copper (I) bromide was set to 3.8 mg, and an amount of pentamethyldiethylenetriamine was set to 4.8 mg.

(Synthesis of Water-Swollen Gel (2-AA Gel) of Polyacrylic Acid Cross-Linked Body)

A water-swollen gel (2-AA gel) of a cylindrical polyacrylic acid cross-linked body having a chemical structure (n=30) in the above Chemical Formula H was obtained in the same manner as in "Synthesis of Water-Swollen Gel (1-AA Gel) of Polyacrylic Acid Cross-Linked Body" in Example 1 except that the poly(tert-butyl acrylate) cross-linked body (2-tBA gel) synthesized above was used instead of poly(tert-butyl acrylate) cross-linked body (1-tBA gel).

(Synthesis of Swollen Gel, which was Swollen to Equilibrium in 0.9% by Weight of Aqueous Solution of Sodium Chloride, of Cross-Linked Body of Partially-Neutralized Polyacrylic Acid (Water Absorbing Resin 2))

A swollen gel, which was swollen to equilibrium in 0.9% by weight of aqueous solution of sodium chloride, of a cross-linked body of partially-neutralized polyacrylic acid (water absorbing resin 2) was obtained in the same manner as in "Synthesis of Swollen Gel, Which Was Swollen to Equilibrium in 0.9% by Weight of Aqueous Solution of Sodium Chloride, of Cross-Linked Body of Partially-Neutralized Polyacrylic Acid (Water Absorbing Resin 1)" in Example 1 except that the water-swollen gel (2-AA gel) of the polyacrylic acid cross-linked body synthesized above was used instead of the water-swollen gel (1-AA gel) of the polyacrylic acid cross-linked body. The swollen gel (water absorbing resin 2) has a chemical structure ($n=30$) in the above Chemical Formula I.

The equilibrium swelling capacity of the swollen gel, which was swollen to equilibrium in 0.9% by weight of aqueous solution of sodium chloride, of the cross-linked body of partially-neutralized polyacrylic acid (water absorbing resin 2) was 38.4 g/g and the elastic modulus thereof was 8,272 Pa. Further, the weight average molecular weight Mw after hydrolysis was 10,473 and the molecular weight distribution Mw/Mn was 1.11. These results are presented in the following Table 1.

Example 3

Synthesis of Four-Arm Star-Shaped Polymer (3-Br)

A solid four-arm star-shaped polymer (3-Br) having a chemical structure ($n=40$) in the above Chemical Formula B was obtained in the same manner as in "Synthesis of Four-Arm Star-Shaped Polymer (1-Br)" in Example 1 except that an amount of tert-butyl acrylate was set to 28.2 g and the reaction time was set to 2 hours.

(Synthesis of Four-Arm Star-Shaped Polymer ($3-N_3$))

A solid four-arm star-shaped polymer ($3-N_3$) having a chemical structure ($n=40$) in the above Chemical Formula C was obtained in the same manner as in "Synthesis of Four-Arm Star-Shaped Polymer ($1-N_3$)" in Example 1 except that the four-arm star-shaped polymer (3-Br) synthesized above was used instead of the four-arm star-shaped polymer (1-Br) and an amount of sodium azide ($NaN_3$) was set to 83 mg.

The weight average molecular weight Mw of the four-arm star-shaped polymer ($3-N_3$) thus obtained was 25,585 and the molecular weight distribution Mw/Mn thereof was 1.11.

(Synthesis of Four-Arm Star-Shaped Polymer (3-Si Alkyne))

A solid four-arm star-shaped polymer (3-Si alkyne) having a chemical structure ($n=40$) in the above Chemical Formula E was obtained in the same manner as in "Synthesis of Four-Arm Star-Shaped Polymer (1-Si Alkyne)" in Example 1 except that the four-arm star-shaped polymer ($3-N_3$) synthesized above was used instead of the four-arm star-shaped polymer ($1-N_3$), an amount of dialkyne was set to 67.3 mg, an amount of copper (I) bromide was set to 28.6 mg, and an amount of pentamethyldiethylenetriamine was set to 38.4 mg.

(Synthesis of Four-Arm Star-Shaped Polymer (3-H Alkyne))

A solid four-arm star-shaped polymer (3-H alkyne) having a chemical structure ($n=40$) in the above Chemical Formula F was obtained in the same manner as in "Synthesis of Four-Arm Star-Shaped Polymer (1-H alkyne)" in Example 1 except that the four-arm star-shaped polymer (3-Si alkyne) synthesized above was used instead of the four-arm star-shaped polymer (1-Si alkyne) and an amount of 1 mol/L tetrahydrofuran solution of tetrabutylammonium fluoride was set to 0.8 ml.

(Synthesis of Poly(tert-Butyl Acrylate) Cross-Linked Body (3-tBA Gel))

A cylindrical poly(tert-butyl acrylate) cross-linked body (3-tBA gel) having a chemical structure ($n=40$) in the above Chemical Formula G was obtained in the same manner as in "Synthesis of Poly(tert-Butyl Acrylate) Cross-Linked Body (1-tBA Gel)" in Example 1 except that 96.1 mg of the four-arm star-shaped polymer ($3-N_3$) synthesized above was used instead of 92.0 mg of the four-arm star-shaped polymer ($1-N_3$), the four-arm star-shaped polymer (3-H alkyne) synthesized above was used instead of the four-arm star-shaped polymer (1-H alkyne), an amount of copper (I) bromide was set to 3.0 mg, and an amount of pentamethyldiethylenetriamine was set to 3.6 mg.

(Synthesis of Water-Swollen Gel (3-AA Gel) of Polyacrylic Acid Cross-Linked Body)

A water-swollen gel (3-AA gel) of a cylindrical polyacrylic acid cross-linked body having a chemical structure ($n=40$) in the above Chemical Formula H was obtained in the same manner as in "Synthesis of Water-Swollen Gel (1-AA Gel) of Polyacrylic Acid Cross-Linked Body" in Example 1 except that the poly(tert-butyl acrylate) cross-linked body (3-tBA gel) synthesized above was used instead of poly(tert-butyl acrylate) cross-linked body (1-tBA gel).

(Synthesis of Swollen Gel, which was Swollen to Equilibrium in 0.9% by Weight of Aqueous Solution of Sodium Chloride, of Cross-Linked Body of Partially-Neutralized Polyacrylic Acid (Water Absorbing Resin 3))

A swollen gel, which was swollen to equilibrium in 0.9% by weight of aqueous solution of sodium chloride, of a cross-linked body of partially-neutralized polyacrylic acid (water absorbing resin 3) was obtained in the same manner as in "Synthesis of Swollen Gel, Which Was Swollen to Equilibrium in 0.9% by Weight of Aqueous Solution of Sodium Chloride, of Cross-Linked Body of Partially-Neutralized Polyacrylic Acid (Water Absorbing Resin 1)" in Example 1 except that the water-swollen gel (3-AA gel) of the polyacrylic acid cross-linked body synthesized above was used instead of the water-swollen gel (1-AA gel) of the polyacrylic acid cross-linked body. The swollen gel (water absorbing resin 3) has a chemical structure ($n=40$) in the above Chemical Formula I.

The equilibrium swelling capacity of the swollen gel, which was swollen to equilibrium in 0.9% by weight of aqueous solution of sodium chloride, of the cross-linked body of partially-neutralized polyacrylic acid (water absorbing resin 3) was 42.5 g/g and the elastic modulus thereof was 7,606 Pa. Further, the weight average molecular weight Mw after hydrolysis was 14,316 and the molecular weight distribution Mw/Mn was 1.11. These results are presented in the following Table 1.

Example 4

Synthesis of Four-Arm Star-Shaped Polymer (4-Br)

A solid four-arm star-shaped polymer (4-Br) having a chemical structure ($n=80$) in the above Chemical Formula B was obtained in the same manner as in "Synthesis of Four-Arm Star-Shaped Polymer (1-Br)" in Example 1 except that an amount of copper (I) bromide was set to 40 mg, an amount of copper (II) bromide was set to 3 mg, an amount of tert-butyl acrylate was set to 28.2 g, an amount of pentamethyldiethylenetriamine was set to 54 mg, an amount of four-arm star-shaped core was set to 0.1 g, and the reaction time was set to 2 hours.

(Synthesis of Four-Arm Star-Shaped Polymer (4-$N_3$))

A solid four-arm star-shaped polymer (4-$N_3$) having a chemical structure (n=80) in the above Chemical Formula C was obtained in the same manner as in "Synthesis of Four-Arm Star-Shaped Polymer (1-$N_3$)" in Example 1 except that the four-arm star-shaped polymer (4-Br) synthesized above was used instead of the four-arm star-shaped polymer (1-Br) and an amount of sodium azide (Na$N_3$) was set to 41 mg.

The weight average molecular weight Mw of the four-arm star-shaped polymer (4-$N_3$) thus obtained was 45,728 and the molecular weight distribution Mw/Mn thereof was 1.16.

(Synthesis of Four-Arm Star-Shaped Polymer (4-Si Alkyne))

A solid four-arm star-shaped polymer (4-Si alkyne) having a chemical structure (n=80) in the above Chemical Formula E was obtained in the same manner as in "Synthesis of Four-Arm Star-Shaped Polymer (1-Si Alkyne)" in Example 1 except that the four-arm star-shaped polymer (4-$N_3$) synthesized above was used instead of the four-arm star-shaped polymer (1-$N_3$), an amount of dialkyne was set to 33.6 mg, an amount of copper (I) bromide was set to 14.3 mg, and an amount of pentamethyldiethylenetriamine was set to 19.2 mg.

(Synthesis of Four-Arm Star-Shaped Polymer (4-H Alkyne))

A solid four-arm star-shaped polymer (4-H alkyne) having a chemical structure (n=80) in the above Chemical Formula F was obtained in the same manner as in "Synthesis of Four-Arm Star-Shaped Polymer (1-H alkyne)" in Example 1 except that the four-arm star-shaped polymer (4-Si alkyne) synthesized above was used instead of the four-arm star-shaped polymer (1-Si alkyne) and an amount of 1 mol/L tetrahydrofuran solution of tetrabutylammonium fluoride was set to 0.4 ml.

(Synthesis of Poly(tert-Butyl Acrylate) Cross-Linked Body (4-tBA Gel))

A cylindrical poly(tert-butyl acrylate) cross-linked body (4-tBA gel) having a chemical structure (n=80) in the above Chemical Formula G was obtained in the same manner as in "Synthesis of Poly(tert-Butyl Acrylate) Cross-Linked Body (1-tBA Gel)" in Example 1 except that 98.0 mg of the four-arm star-shaped polymer (4-$N_3$) synthesized above was used instead of 92.0 mg of the four-arm star-shaped polymer (1-$N_3$), the four-arm star-shaped polymer (4-H alkyne) synthesized above was used instead of the four-arm star-shaped polymer (1-H alkyne), an amount of copper (I) bromide was set to 1.5 mg, and an amount of pentamethyldiethylenetriamine was set to 1.8 mg.

(Synthesis of Water-Swollen Gel (4-AA Gel) of Polyacrylic Acid Cross-Linked Body)

A water-swollen gel (4-AA gel) of a cylindrical polyacrylic acid cross-linked body having a chemical structure (n=80) in the above Chemical Formula H was obtained in the same manner as in "Synthesis of Water-Swollen Gel (1-AA Gel) of Polyacrylic Acid Cross-Linked Body" in Example 1 except that the poly(tert-butyl acrylate) cross-linked body (4-tBA gel) synthesized above was used instead of poly(tert-butyl acrylate) cross-linked body (1-tBA gel).

(Synthesis of Swollen Gel, which was Swollen to Equilibrium in 0.9% by Weight of Aqueous Solution of Sodium Chloride, of Cross-Linked Body of Partially-Neutralized Polyacrylic Acid (Water Absorbing Resin 4))

A swollen gel, which was swollen to equilibrium in 0.9% by weight of aqueous solution of sodium chloride, of a cross-linked body of partially-neutralized polyacrylic acid (water absorbing resin 4) was obtained in the same manner as in "Synthesis of Swollen Gel, Which Was Swollen to Equilibrium in 0.9% by Weight of Aqueous Solution of Sodium Chloride, of Cross-Linked Body of Partially-Neutralized Polyacrylic Acid (Water Absorbing Resin 1)" in Example 1 except that the water-swollen gel (4-AA gel) of the polyacrylic acid cross-linked body synthesized above was used instead of the water-swollen gel (1-AA gel) of the polyacrylic acid cross-linked body. The swollen gel (water absorbing resin 4) has a chemical structure (n=80) in the above Chemical Formula I.

The equilibrium swelling capacity of the swollen gel, which was swollen to equilibrium in 0.9% by weight of aqueous solution of sodium chloride, of the cross-linked body of partially-neutralized polyacrylic acid (water absorbing resin 4) was 80.4 g/g and the elastic modulus thereof was 1,308 Pa. Further, the weight average molecular weight Mw after hydrolysis was 24,725 and the molecular weight distribution Mw/Mn was 1.14. These results are presented in the following Table 1.

Comparative Example 1

17.170 g of 48% by mass aqueous solution of sodium hydroxide and 21.750 g of pure water which has been cooled to 5° C. were put in a polypropylene vessel (manufactured by TGK) having a capacity of 250 ml and stirred. A mixture solution of 0.144 g of polyethylene glycol diacrylate (molecular weight (Mw) of 523) and 19.800 g of acrylic acid was slowly added thereto to prepare a reaction solution. Then, the reaction solution was degassed for 20 minutes under a nitrogen gas atmosphere. Subsequently, 0.650 g of 10% by mass aqueous solution of sodium persulfate and 0.484 g of 0.1% by mass aqueous solution of L-ascorbic acid were added to the reaction solution while stirring. The obtained reaction solution was transferred swiftly to the following reactor vessel replaced with nitrogen gas by using a syringe and left to stand still in a drying machine having a temperature of 60° C. for 18 hours to obtain a disk-shaped gel. The above-described reactor vessel is an apparatus in which silicon rubber having a circular hole is interposed between two glass plates and the circumference thereof is fixed with clips.

Some (2.0 g) of the gel was cut into a strip, transferred into a polypropylene vessel with a lid (manufactured by EnTech, Inc.) having a capacity of 780 ml, immersed in 400 ml of 0.9% by weight aqueous solution of sodium chloride and left to stand still for 48 hours. Thereafter, the aqueous solution was removed in the polypropylene vessel, and 400 ml of 0.9% by weight aqueous solution of sodium chloride was added again, and left to stand still for 48 hours. After that, the aqueous solution was removed in the polypropylene vessel, and 400 ml of 0.9% by weight aqueous solution of sodium chloride was added again thereto, followed by being left to stand still for 48 hours. In this way, a swollen gel, which was swollen to equilibrium in 0.9% by weight of aqueous solution of sodium chloride, of the cross-linked body of partially-neutralized polyacrylic acid (comparative water absorbing resin 1) of this Comparative Example was obtained.

The equilibrium swelling capacity of the swollen gel, which was swollen to equilibrium in 0.9% by weight of aqueous solution of sodium chloride, of the cross-linked body of partially-neutralized polyacrylic acid (comparative water absorbing resin 1) of this Comparative Example was 33.5 g/g and the elastic modulus thereof was 7,867 Pa.

Further, the weight average molecular weight (Mw) after hydrolysis was 1,460,000 and the molecular weight distribution (Mw/Mn) was 1.69. These results are presented in the following Table 1.

Comparative Example 2

A swollen gel, which was swollen to equilibrium in 0.9% by weight of aqueous solution of sodium chloride, of the cross-linked body of partially-neutralized polyacrylic acid (comparative water absorbing resin 2) of this Comparative Example was obtained in the same manner as in Comparative Example 1 except that an amount of polyethylene glycol diacrylate was set to 0.058 g and an amount of pure water was set to 21.836 g.

The equilibrium swelling capacity of the swollen gel, which was swollen to equilibrium in 0.9% by weight of aqueous solution of sodium chloride, of the cross-linked body of partially-neutralized polyacrylic acid (comparative water absorbing resin 2) of this Comparative Example was 37.3 g/g and the elastic modulus thereof was 5,910 Pa. Further, the weight average molecular weight (Mw) after hydrolysis was 1,370,000 and the molecular weight distribution (Mw/Mn) was 1.56. These results are presented in the following Table 1.

Comparative Example 3

A swollen gel, which was swollen to equilibrium in 0.9% by weight of aqueous solution of sodium chloride, of the cross-linked body of partially-neutralized polyacrylic acid (comparative water absorbing resin 3) of this Comparative Example was obtained in the same manner as in Comparative Example 1 except that an amount of polyethylene glycol diacrylate was set to 0.043 g and an amount of pure water was set to 21.851 g.

The equilibrium swelling capacity of the swollen gel, which was swollen to equilibrium in 0.9% by weight of aqueous solution of sodium chloride, of the cross-linked body of partially-neutralized polyacrylic acid (comparative water absorbing resin 3) of this Comparative Example was 44.5 g/g and the elastic modulus thereof was 3,541 Pa. Further, the weight average molecular weight (Mw) after hydrolysis was 1,440,000 and the molecular weight distribution (Mw/Mn) was 1.52. These results are presented in the following Table 1.

Comparative Example 4

A swollen gel, which was swollen to equilibrium in 0.9% by weight of aqueous solution of sodium chloride, of the cross-linked body of partially-neutralized polyacrylic acid (comparative water absorbing resin 4) of this Comparative Example was obtained in the same manner as in Comparative Example 1 except that an amount of polyethylene glycol diacrylate was set to 0.028 g and an amount of pure water was set to 21.866 g.

The equilibrium swelling capacity of the swollen gel, which was swollen to equilibrium in 0.9% by weight of aqueous solution of sodium chloride, of the cross-linked body of partially-neutralized polyacrylic acid (comparative water absorbing resin 4) of this Comparative Example was 65.5 g/g and the elastic modulus thereof was 980 Pa. Further, the weight average molecular weight (Mw) after hydrolysis was 1,340,000 and the molecular weight distribution (Mw/Mn) was 1.56. These results are presented in the following Table 1.

Comparative Example 5

A swollen gel, which was swollen to equilibrium in 0.9% by weight of aqueous solution of sodium chloride, of the cross-linked body of partially-neutralized polyacrylic acid (comparative water absorbing resin 5) of this Comparative Example was obtained in the same manner as in Comparative Example 1 except that an amount of 10% by mass aqueous solution of sodium persulfate was set to 3.250 g, an amount of 0.1% by mass aqueous solution of L-ascorbic acid was set to 2.420 g, and an amount of pure water was set to 17.170 g.

The equilibrium swelling capacity of the swollen gel, which was swollen to equilibrium in 0.9% by weight of aqueous solution of sodium chloride, of the cross-linked body of partially-neutralized polyacrylic acid (comparative water absorbing resin 5) of this Comparative Example was 31.7 g/g and the elastic modulus thereof was 9,328 Pa. Further, the weight average molecular weight (Mw) after hydrolysis was 927,682 and the molecular weight distribution (Mw/Mn) was 1.85. These results are presented in the following Table 1.

Comparative Example 6

A swollen gel, which was swollen to equilibrium in 0.9% by weight of aqueous solution of sodium chloride, of the cross-linked body of partially-neutralized polyacrylic acid (comparative water absorbing resin 6) of this Comparative Example was obtained in the same manner as in Comparative Example 1 except that an amount of pure water was set to 17.170 g and 2.970 g of 10% by mass aqueous solution of hydrogen phosphite disodium pentahydrate was added at the same time of addition of 10% by mass of aqueous solution of sodium persulfate and 0.1% by mass of aqueous solution of L-ascorbic acid.

The equilibrium swelling capacity of the swollen gel, which was swollen to equilibrium in 0.9% by weight of aqueous solution of sodium chloride, of the cross-linked body of partially-neutralized polyacrylic acid (comparative water absorbing resin 6) of this Comparative Example was 33.1 g/g and the elastic modulus thereof was 8,421 Pa. Further, the weight average molecular weight (Mw) after hydrolysis was 1,116,000 and the molecular weight distribution (Mw/Mn) was 1.49. These results are presented in the following Table 1.

Comparative Example 7

In a polypropylene vessel having a capacity of 120 ml, 20.00 g of 30% by mass aqueous solution of sodium polyacrylate (DL522, produced by NIPPON SHOKUBAI CO., LTD.) was added to 0.111 g of ethylene glycol diglycidyl ether (Denacol EX-810, produced by Nagase ChemteX Corporation) and dissolved by stirring with a spatula. Thereafter, the polypropylene vessel was covered with a lid and left to stand still for 3 hours so as to remove air bubbles in the solution. The polypropylene vessel was put in an oven having a temperature of 80° C. and left to stand still for 12 hours to obtain a disk-shaped gel.

The gel was transferred into a polypropylene vessel with a lid (manufactured by EnTech, Inc.) having a capacity of 780 ml, immersed in a mixture solution of 8 ml of 2 mol/l aqueous solution of hydrochloric acid and 192 ml of 0.9% by weight aqueous solution of sodium chloride, and left to stand still for 72 hours. Thereafter, the aqueous solution was removed in the polypropylene vessel, and 200 ml of 0.9% by weight aqueous solution of sodium chloride was added again thereto, followed by being left to stand still for 48 hours. After that, the aqueous solution was removed in the polypropylene vessel, and 200 ml of 0.9% by weight aqueous solution of sodium chloride was added again thereto, followed by being left to stand still for 48 hours. The aqueous solution was further removed again from the polypropylene vessel and added again with 200 ml of 0.9% by weight aqueous solution of sodium chloride and left to stand still for 48 hours. In this way, a swollen gel, which was swollen to equilibrium in 0.9% by weight of aqueous solution of sodium chloride, of the cross-linked body of partially-neutralized polyacrylic acid (comparative water absorbing resin 7) of this Comparative Example was obtained.

The equilibrium swelling capacity of the swollen gel, which was swollen to equilibrium in 0.9% by weight of aqueous solution of sodium chloride, of the cross-linked body of partially-neutralized polyacrylic acid (comparative water absorbing resin 7) of this Comparative Example was 51.8 g/g and the elastic modulus thereof was 3,149 Pa. Further, the weight average molecular weight (Mw) after hydrolysis was 239,600 and the molecular weight distribution (Mw/Mn) was 3.48. These results are presented in the following Table 1.

Comparative Example 8

The CRC and the weight average molecular weight (Mw) after hydrolysis of various water absorbing resins are described in Examples and Comparative Examples of Japanese Patent Application National Publication (Laid-Open) No. 2009-531467, which is one of the above-described prior art documents. Among these, in the water absorbing resin having the highest "reference cross-linked structure index" represented by the following Mathematical Formula 2, CRC was 28.3 (g/g), the weight average molecular weight (Mw) after hydrolysis was 221,634, and the molecular weight distribution (Mw/Mn) was 1.95. This water absorbing resin is used as a comparative water absorbing resin 8 and these results are presented in the following Table 1.

$$\text{Reference cross-linked structure index} = (CRC)^{1/3} / (\text{weight average molecular weight (Mw) after hydrolysis}) \times 1{,}000{,}000 \quad [\text{Mathematical Formula 2}]$$

TABLE 1

| | Water absorbing resin | Weight average molecular weight after hydrolysis treatment Mw | Molecular weight distribution after hydrolysis treatment Mw/Mn | Equilibrium swelling capacity with respect to 0.9% by weight of brine (g/g) | Elastic modulus (Pa) | Cross-linked structure index |
|---|---|---|---|---|---|---|
| Example 1 | Water absorbing resin 1 | 7,355 | 1.06 | 24.8 | 24,276 | 397.58 |
| Example 2 | Water absorbing resin 2 | 10,473 | 1.11 | 38.4 | 8,272 | 322.14 |
| Example 3 | Water absorbing resin 3 | 14,316 | 1.11 | 42.5 | 7,606 | 243.77 |
| Example 4 | Water absorbing resin 4 | 24,725 | 1.14 | 80.4 | 1,308 | 174.56 |
| Comparative Example 1 | Comparative water absorbing resin 1 | 1,460,000 | 1.69 | 33.5 | 7,867 | 2.21 |
| Comparative Example 2 | Comparative water absorbing resin 2 | 1,370,000 | 1.56 | 37.3 | 5,910 | 2.44 |
| Comparative Example 3 | Comparative water absorbing resin 3 | 1,440,000 | 1.52 | 44.5 | 3,541 | 2.46 |
| Comparative Example 4 | Comparative water absorbing resin 4 | 1,340,000 | 1.56 | 65.5 | 980 | 3.01 |
| Comparative Example 5 | Comparative water absorbing resin 5 | 927,682 | 1.85 | 31.7 | 9,328 | 3.41 |
| Comparative Example 6 | Comparative water absorbing resin 6 | 1,116,000 | 1.49 | 33.1 | 8,421 | 2.88 |
| Comparative Example 7 | Comparative water absorbing resin 7 | 239,600 | 3.48 | 51.8 | 3,149 | 15.56 |
| Comparative Example 8 | Comparative water absorbing resin 8 | 221,634 | 1.95 | 28.3*[1] | — | 13.75*[2] |

*[1]This value is not an equilibrium swelling capacity with respect to 0.9% by weight of brine but CRC.
*[2]This value is not a cross-linked structure index but a reference cross-linked structure index From the results presented in Table 1 and FIG. 3, it was found that the water absorbing resins of Examples 1 to 4 according to the present invention exhibited a high elastic modulus of the swollen gel compared to the water absorbing resins exhibiting the same equilibrium swelling capacity according to Comparative Examples. In addition, it was found that, in Examples 1 to 4, the cross-linked structure index decreased as the weight average molecular weight (Mw) after the hydrolysis treatment increased. It is considered that a water absorbing resin, which is synthesized using a star-shaped polymer having a reactive functional group at the terminal and having a further larger molecular weight as a starting material according to the same procedure as in Examples 1 to 4, exhibits a further larger weight average molecular weight (Mw) after the hydrolysis treatment and a further smaller cross-linked structure index. It is considered that the water absorbing resin thus obtained has little entanglement or few dangling chains as is the case with Examples 1 to 4 and exhibits a high elastic modulus of the swollen gel compared to the water absorbing resins exhibiting the same equilibrium swelling capacity according to Comparative Examples. In other words, it is believed that it is possible to obtain a water absorbing resin which has a larger weight average molecular weight (Mw) after the hydrolysis treatment and a smaller cross-linked structure index than those of Examples 1 to 4 and exhibits a high elastic modulus of the swollen gel compared to the water absorbing resins exhibiting the same equilibrium swelling capacity according to Comparative Examples.

In view of these, when the water absorbing resin exhibits a cross-linked structure index value of 14 or more (preferably 170 or more), a weight average molecular weight (Mw) after the hydrolysis treatment of 220,000 or less, and a molecular weight distribution (Mw/Mn) of 3.40 or less, it can be expected that the water absorbing resin exhibits a high elastic modulus of the swollen gel compared to the water absorbing resins exhibiting the same equilibrium swelling capacity according to Comparative Examples. According to this, the water absorbing resin according to the present invention can exhibit an excellent liquid permeability even under a load, compared to a conventional water absorbing resin formed from a cross-linked body of partially neutralized polyacrylic acid (salt).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbing article comprising water absorbing resin, the water absorbing resin comprising a water-soluble unsaturated monomer, which has a dissociable group, as a main component in a repeating unit of a main chain and having an internal cross-linked structure,
    wherein a cross-linked structure index represented by the following Mathematical Formula 1 is 170 or more,
    a weight average molecular weight (Mw) after hydrolysis treatment is 220,000 or less, and
    a molecular weight distribution (Mw/Mn) after hydrolysis treatment is 1.00 or more but 3.40 or less:

$$\text{Cross-linked structure index} = (\text{Equilibrium swelling capacity with respect to 0.9\% by weight of brine})^{1/3}/(\text{Weight average molecular weight (Mw) after hydrolysis treatment}) \times 1,000,000,$$
[Mathematical Formula 1]

wherein the hydrolysis treatment is treatment in which 50 mg of the water absorbing resin as a solid content is left to stand still in 10 g of 0.1 mol/l aqueous solution of sodium hydroxide at 80° C. for 3 weeks, and the weight average molecular weight (Mw) is a value obtained by measurement after the treatment.

2. The absorbing article of claim 1, wherein, in the water absorbing resin, 90 mol % or more of the repeating unit is a repeating unit derived from a water-soluble unsaturated monomer having a carboxylic acid (salt) group as a dissociable group.

3. The absorbing article of claim 1, wherein, in the water absorbing resin, 90 mol % or more of the repeating unit is a repeating unit derived from acrylic acid (salt).

4. The absorbing article of claim 1, wherein, in the water absorbing resin, a neutralization ratio is 50 to 100 mol %.

5. The absorbing article of claim 1, wherein the water absorbing resin is in the form of water absorbing resin particles.

6. The absorbing article of claim 1, wherein the absorbing article comprises an absorbing core and wherein the water absorbing resin is comprised by the absorbing core, the absorbing core not comprising any cellulose fibers.

* * * * *